US012268503B2

(12) United States Patent
Grzelak et al.

(10) Patent No.: US 12,268,503 B2
(45) Date of Patent: Apr. 8, 2025

(54) PATIENT'S SKIN-PUNCTURING DEVICES

(71) Applicant: HTL-STREFA S.A., Ozorków (PL)

(72) Inventors: Robert Grzelak, Ozorków (PL);
Marcin Rozwadowski, Ozorków (PL);
Jacek Karbowniczek, Ozorków (PL);
Marcin Komuda, Ozorków (PL);
Marcin Niemiec, Ozorków (PL)

(73) Assignee: HTL-STREFA S.A., Ozorków (PL)

( * ) Notice: Subject to any disclaimer, the term of this patent is extended or adjusted under 35 U.S.C. 154(b) by 714 days.

(21) Appl. No.: 16/643,404

(22) PCT Filed: Sep. 1, 2018

(86) PCT No.: PCT/PL2018/050046
§ 371 (c)(1),
(2) Date: Feb. 28, 2020

(87) PCT Pub. No.: WO2019/045580
PCT Pub. Date: Mar. 7, 2019

(65) Prior Publication Data
US 2021/0068728 A1 Mar. 11, 2021

(30) Foreign Application Priority Data

Sep. 2, 2017 (PL) .................................. 422730

(51) Int. Cl.
A61B 5/151 (2006.01)
A61B 5/15 (2006.01)

(52) U.S. Cl.
CPC .... A61B 5/15117 (2013.01); A61B 5/150198 (2013.01); A61B 5/150412 (2013.01);
(Continued)

(58) Field of Classification Search
CPC ........ A61B 5/150198; A61B 5/150412; A61B 5/15113; A61B 5/15117; A61B 5/1513; A61B 5/150183
See application file for complete search history.

(56) References Cited

U.S. PATENT DOCUMENTS 5,984,940 A 11/1999 Davis et al.
2008/0027474 A1* 1/2008 Curry ............... A61B 5/150519
606/181
(Continued)

FOREIGN PATENT DOCUMENTS

EP 2220999 A1 8/2010
EP 2375985 B1 10/2011
(Continued)

OTHER PUBLICATIONS

International Search Report and Written Opinion of the International Searching Authority, mailed Dec. 20, 2018, in corresponding International Application No. PCT/PL2018/050046 (Authorized Officer, Ottmar Schultz), 11 pages.

Primary Examiner — Rene T Towa
Assistant Examiner — Huong Q Nguyen
(74) Attorney, Agent, or Firm — MH2 Technology Law Group LLP

(57) ABSTRACT

A skin-puncturing device may include: a main body; a cup configured to close the main body; a puncturing mechanism with a lancet guiding unit; a drive spring of the lancet guiding unit; a driving sleeve; a return spring of the lancet guiding unit; a button configured to tension the drive spring; a member configured to release the tension of the drive spring; a puncture depth regulation mechanism; and a used lancet removal mechanism. The driving sleeve may be configured to rotate within the casing, to slide toward a front part of the device, and to slide toward a back part of the device. The puncture depth regulation mechanism may
(Continued)

Figure 1:
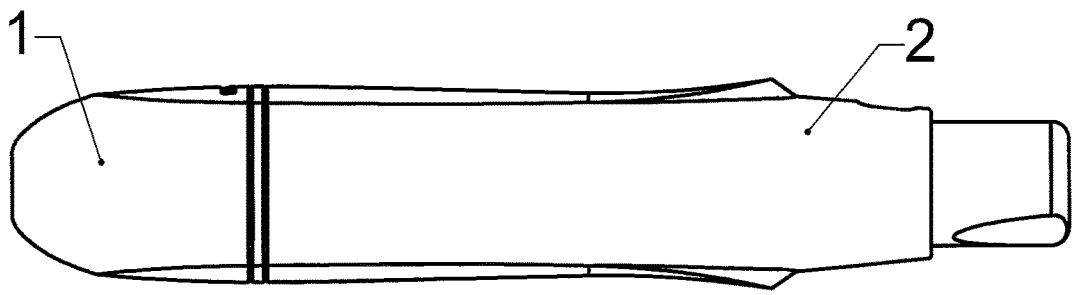

include: the button, rotary-coupled with the driving sleeve; limiting steps that define relative puncture depths for selection by the driving sleeve; and a bumper of the driving sleeve configured to engage a selected one of the limiting steps.

20 Claims, 28 Drawing Sheets

(52) U.S. Cl.
CPC ........ *A61B 5/15113* (2013.01); *A61B 5/1513* (2013.01); *A61B 5/150022* (2013.01); *A61B 5/15019* (2013.01); *A61B 5/150503* (2013.01); *A61B 5/15194* (2013.01)

(56) References Cited

U.S. PATENT DOCUMENTS

| | | | | |
|---|---|---|---|---|
| 2009/0299398 | A1* | 12/2009 | Yoritaka | A61B 5/15117 606/182 |
| 2010/0049234 | A1* | 2/2010 | Kitamura | A61B 5/1519 606/182 |
| 2010/0241149 | A1* | 9/2010 | Nishiyama | A61B 5/150412 606/181 |

FOREIGN PATENT DOCUMENTS

| | | |
|---|---|---|
| EP | 2375986 B1 | 10/2011 |
| WO | 2012/046851 A1 | 4/2012 |
| WO | 2013/155052 A1 | 10/2013 |

* cited by examiner

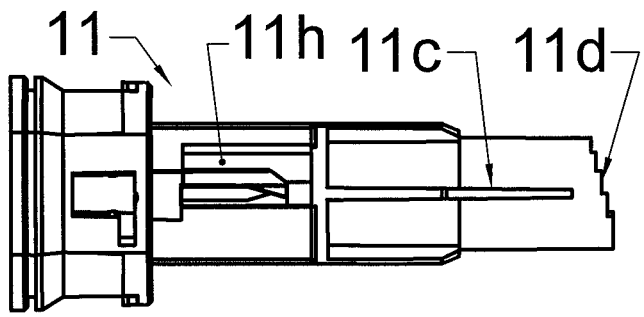
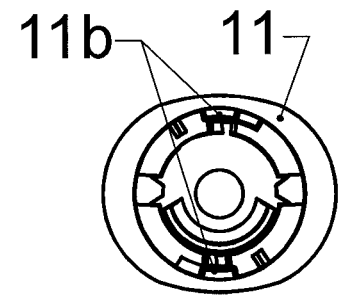
Fig.22  Fig.24
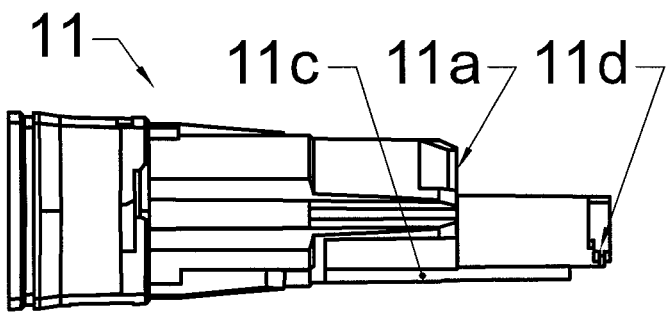
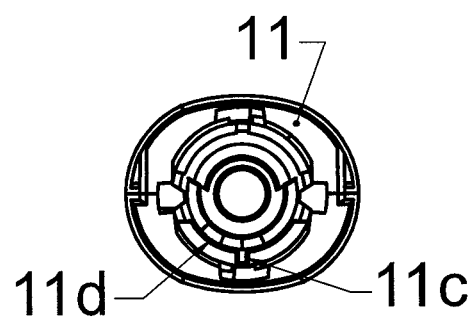
Fig.23  Fig.25
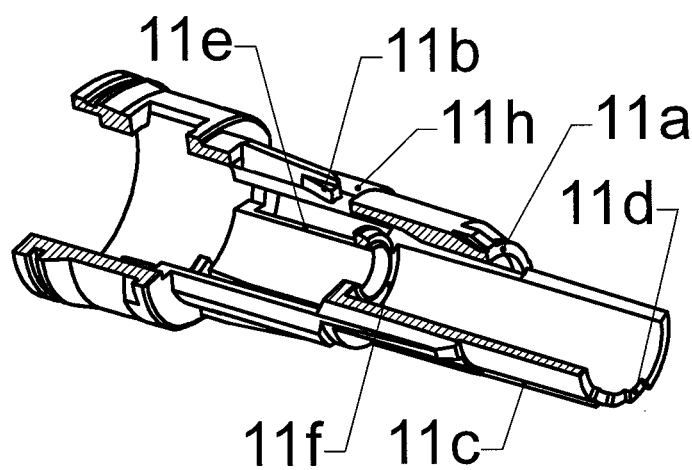
Fig.26
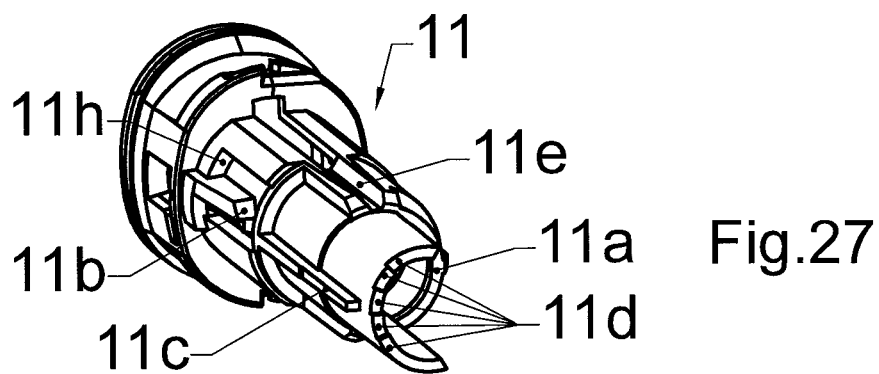
Fig.27 view a view b view c view d

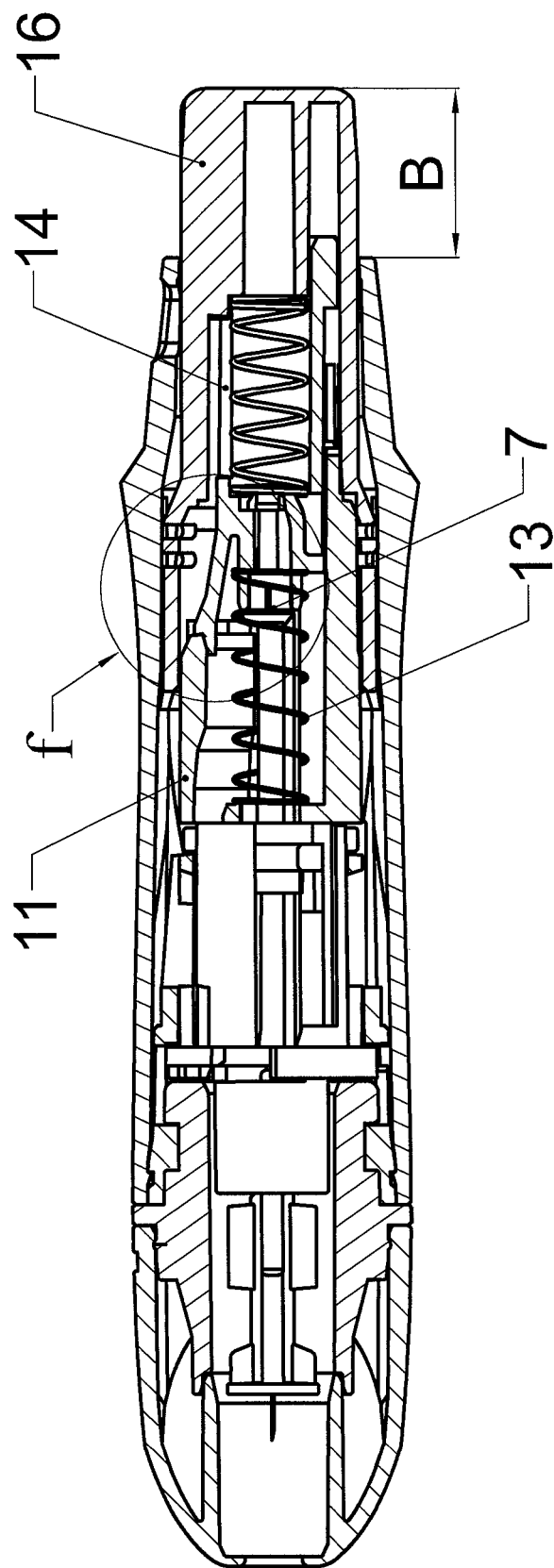
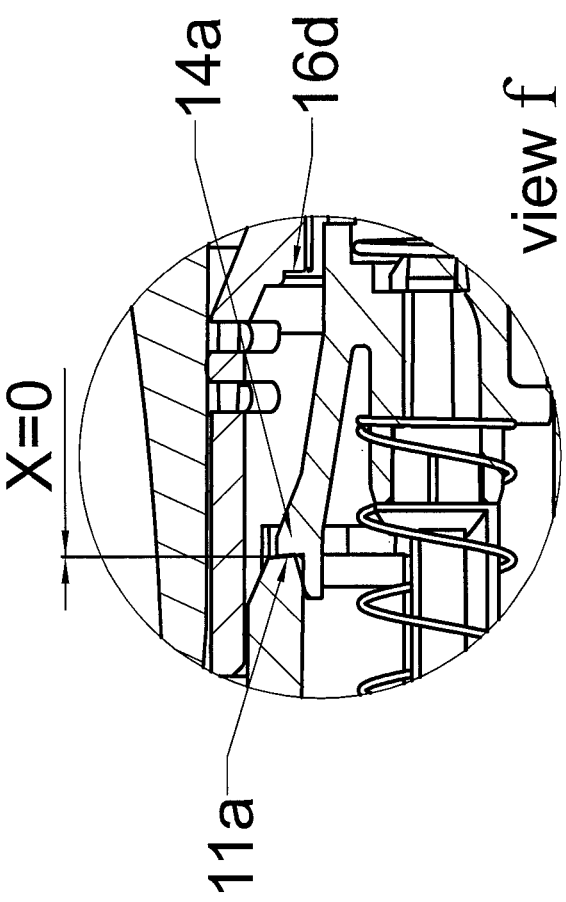
Fig.79
Fig.80 view f view h

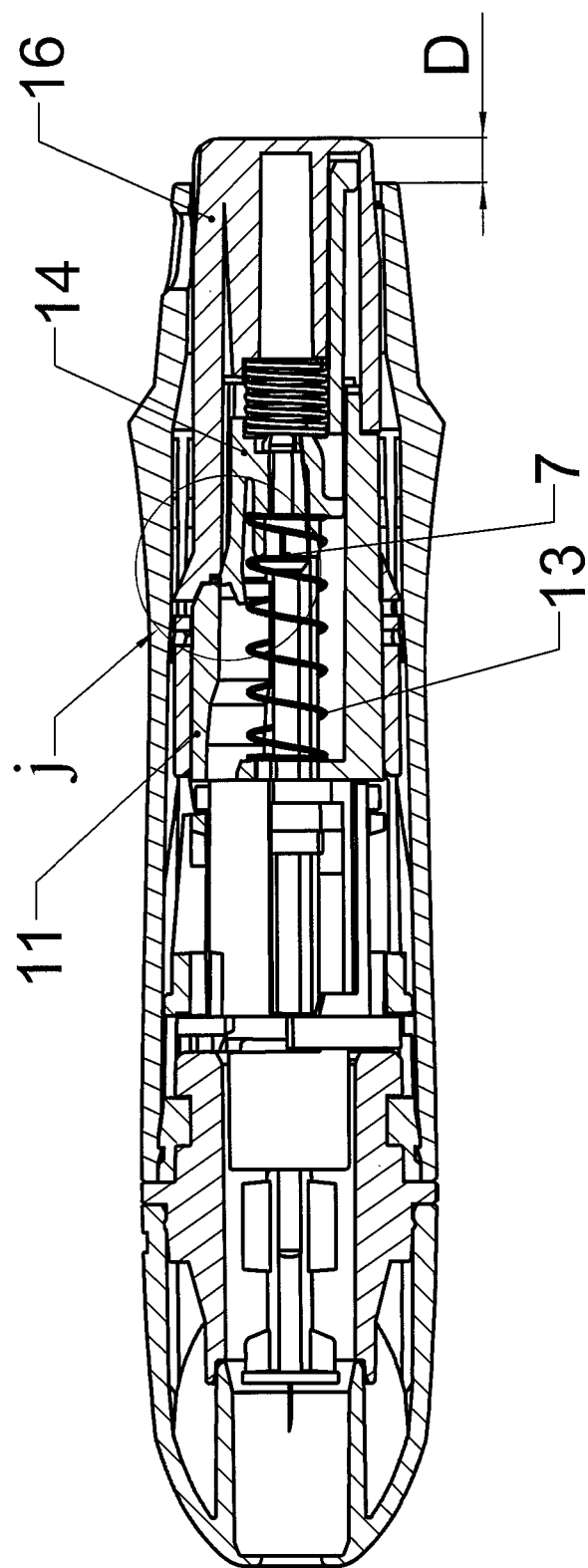
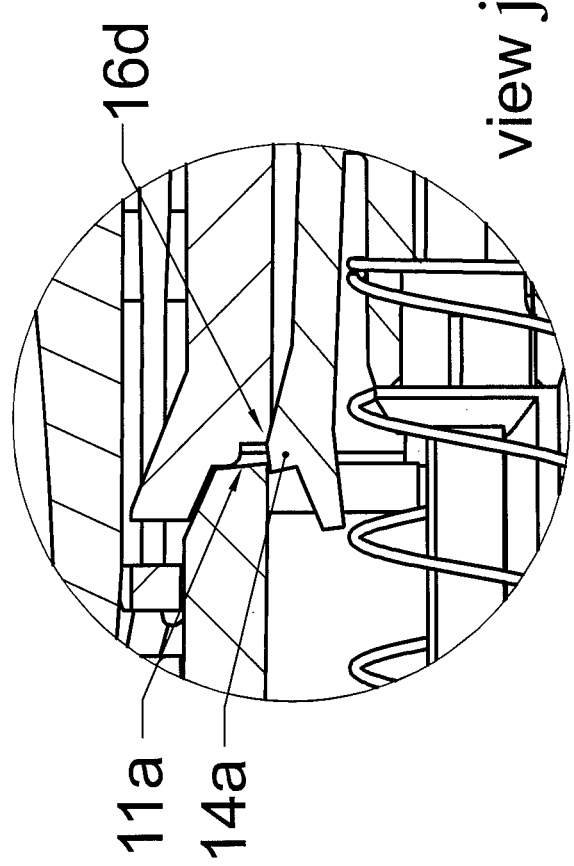

view k

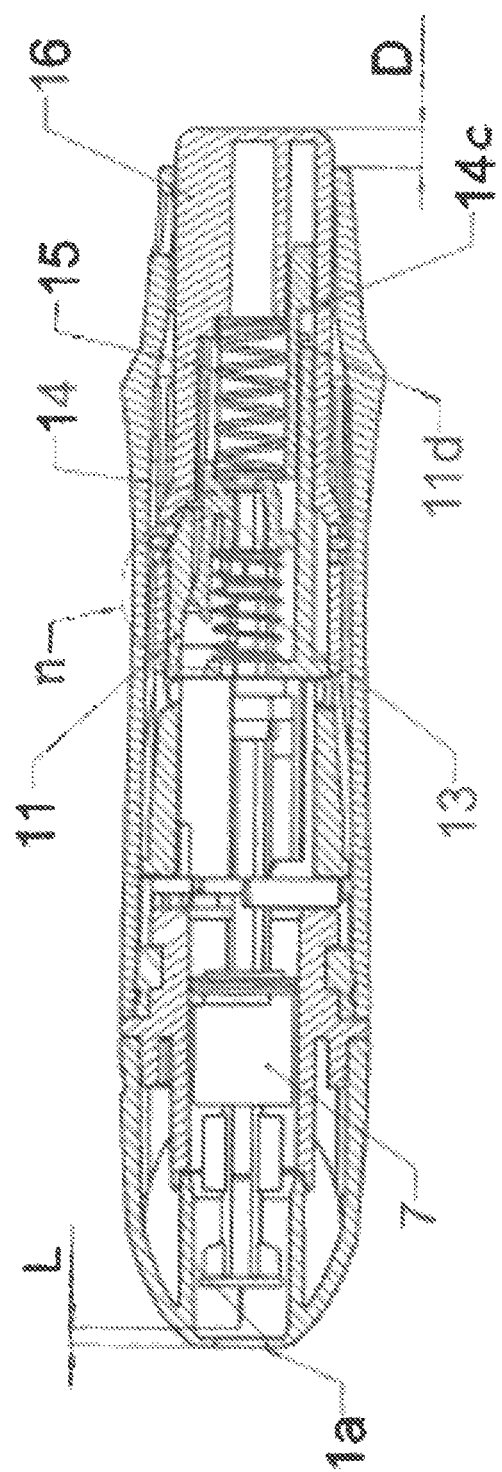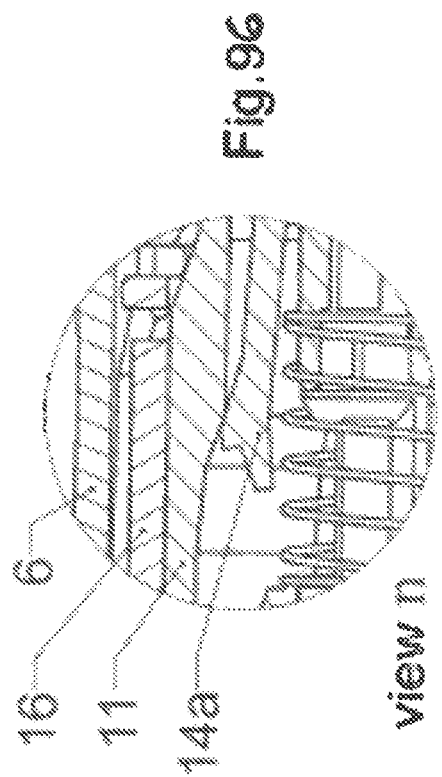

PATIENT'S SKIN-PUNCTURING DEVICES

CROSS-REFERENCE TO RELATED APPLICATION(S)

This application is a national stage entry from International Application No. PCT/PL2018/050046, filed on Sep. 1, 2018, in the Receiving Office ("RO/PL") of the Polish Patent Office ("PPO"), published as International Publication No. WO 2019/045580 A1 on Mar. 7, 2019; International Application No. PCT/PL2018/050046 claims priority under 35 U.S.C. § 119 from Polish Patent Application No. P.422730, filed on Sep. 2, 2017, in the PPO; the entire contents of all of these applications are incorporated herein by reference.

The subject of the invention is the patient's skin puncturing device, which is designed especially for blood sampling.

Puncturing devices, equipped with disposable lancets, designed to puncture human skin in order to sample a drop of capillary blood for medical tests, for instance level of glucose, are known and widely used. Most of these devices are comprised of casing and lancet cover, lancet carrier, loading mechanism that loads one of the springs, activating mechanism that releases the loaded spring and lever or slide that pushes the lancet out. Lancet is launched from retracted position, from within the device ahead, to the position where only a fragment of the lancet needle pokes out of the front surface, which is put against the skin. Some devices of this sort have a puncture depth regulation mechanism. The key feature of the puncturing device is simplicity of use and handling comfort, because older diabetic patients, who might have problems with sight and firm grip, are the biggest group of users of such devices. Therefore, the construction of such devices aims to create shape and manner of operating similar to a typical pen, thus a device of proven, simple and intuitive shape, well known to everyone.

In the descriptions of European patents no. EP2375985 and EP2375986 two types of patient's skin puncturing devices were disclosed, equipped with oblong body, shut from the front with a cup, from which the lancet blade protrudes, drive spring and return spring, puncture depth regulating mechanism with regulation wheel at the back of the body, side slider that loads the drive spring and side button that releases the spring.

In publication WO 2013/155052 a puncturing device similar to a pen was disclosed, equipped with drive spring, return spring, spring loading button at the back of the device body, front cup, from which the lancet blade protrudes, side button releasing the spring and side slider ejects the used lancet.

The goal of the invention was to develop a construction of the patient's skin puncturing device with a minimized number of elements controlling the device.

This goal is met by a device according to the invention, equipped with oblong main body and a cup closing the front end of the main body, with an opening for puncturing lancet blade, put to the patient's skin. This device further comprises a puncturing mechanism with a lancet guiding unit, drive spring of the lancet guiding unit, return spring of the lancet guiding unit, button for loading the drive spring at the back of the main body and triggering member releasing the drive spring, as well as a mechanism adjusting the puncture depth and mechanism for ejecting the used lancet. The invention consists of that the main body of the device has a casing in form of a tube with longitudinal axis as well as with open front and back end. The puncturing mechanism, the puncture depth regulation mechanism and used lancet removal mechanism constitute the mechanism unit, located inside the main body. The elements of the mechanism unit are placed in mechanism body, fitted immovably inside the casing. The mechanism body has the front end, generally flush with the front end of the body and the back end, located inside of the body. The lancet guiding unit is comprised of a lancet socket with oblong guide that passes through an opening in the cross partition of the mechanism body and a lancet chamber in the front. At the back end, the guide is connected with the front end of a driving sleeve. The driving sleeve is mounted rotary and sliding in the back end of the mechanism body. The return spring is located between the transverse partition of the mechanism body and the end of the driving sleeve, which is connected with the lancet socket guide. The drive spring is located between the driving sleeve and the button. The button is sliding and rotary fitted in the back of the casing. The triggering member the mainspring is a springy latch of the drive sleeve that cooperates with stop surface of the mechanism body and activating surface of the button. The puncture depth regulation mechanism is comprised of a button rotary coupled with the driving sleeve and limiting steps limiting the movement of the bumper of the driving sleeve.

In one of variants of the invention, the button is equipped with at least one catch, defining the sequence of angular positions of the button during its rotation against the body and a sequence of anti-rotary notches opposite of the longitudinal fin of the mechanism body in every angular position of the button, defined by the catch. The button is linked to two sliders, fitted sliding inside channels of the mechanism body, whereby the front latches of the side sliders reach into the mechanism body. In the inner part of the mechanism body there is a rotary fitted setting of inner driver, in which the driver is fitted sliding longitudinally, with notches for front latches of the side sliders. The cup has a longitudinal channel for the lancet chamber, bayonet connector elements of the cup cooperating with elements of the bayonet connector in the front part of the main body and at least one coupling fin with the setting of driver. The next variant of the invention, the used lancet removal mechanism is comprised of ejector fitted sliding on the lancet socket guide between the lancet chamber and the driver, and throughfeed window for ejector, located at the bottom of the lancet chamber, button, driving sleeve, return spring and driver.

In another variant of the invention, the cup is comprised of the cup sheath and immovable cup base fitted in the cup sheath, while the longitudinal channel, elements of the bayonet connector and at least one fin are the integral parts of the cup base.

In next variant of the invention, the device is equipped with indicator of selected angular position of the button in relation to the casing.

In another variant of the invention, the selected angular position indicator of the button is a sequence of symbols of the angular positions of the button, located circumferentially on the side surface and a window in the body, located above the said symbols on the button in its released state.

In another variant of the invention the end of the button protruding from the body and the cup, have a surface for the operator's finger, indicated by the change of the outer curvature of the button and the cup surface, whereas the outer surface of the body has an elevated shape improving operator's grip.

The device, according to the invention, might be used with single hand and it has only two elements that the user shall interact with, namely the button at the end of the body and the cup at the front side of the body. In order to perform the puncture, the operator only has to use one finger, to push the button. After releasing the button, the device is ready to perform another puncture. The possibility of an accidental puncture occurring is minimized when the cup is not fitted, which definitely increases the safety of the user while changing the lancet. Only one outer element is movable, i.e. the button, which radically minimizes the possibility of damage by breaking, tearing off or falling out of any element. Tight casing with minimized number of slits helps keeping the device clean. One distinct actuator, that is the button, simplifies the personalization with application of button in various colors.

Figure 2:
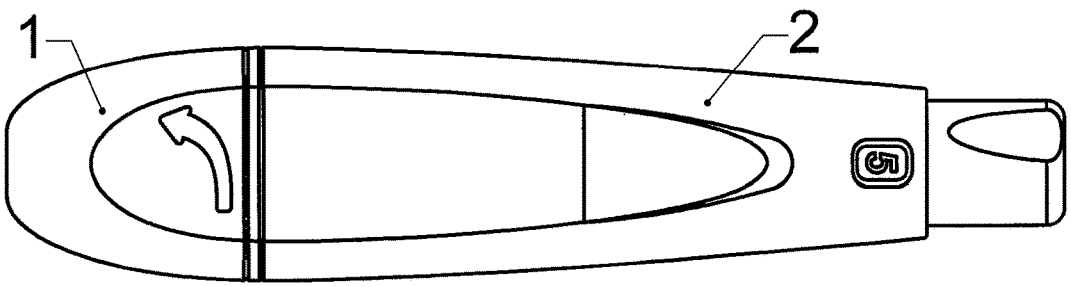
Figure 3:
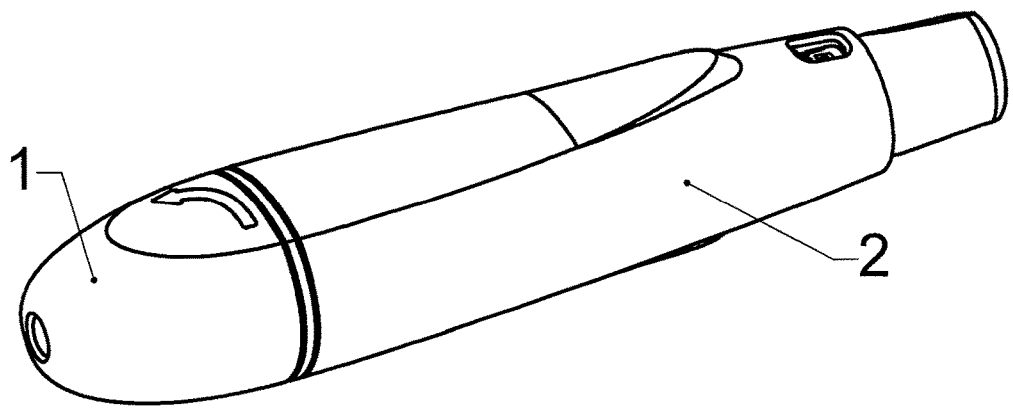
Figure 4:
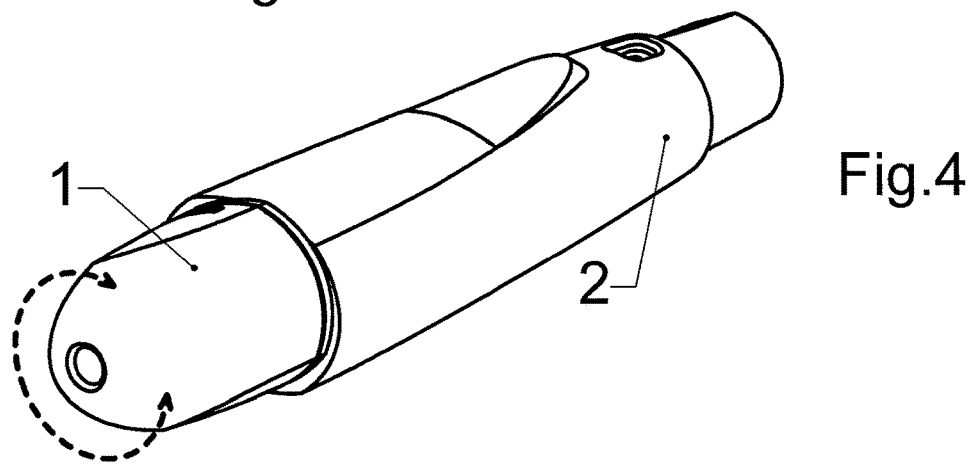
Figure 5:
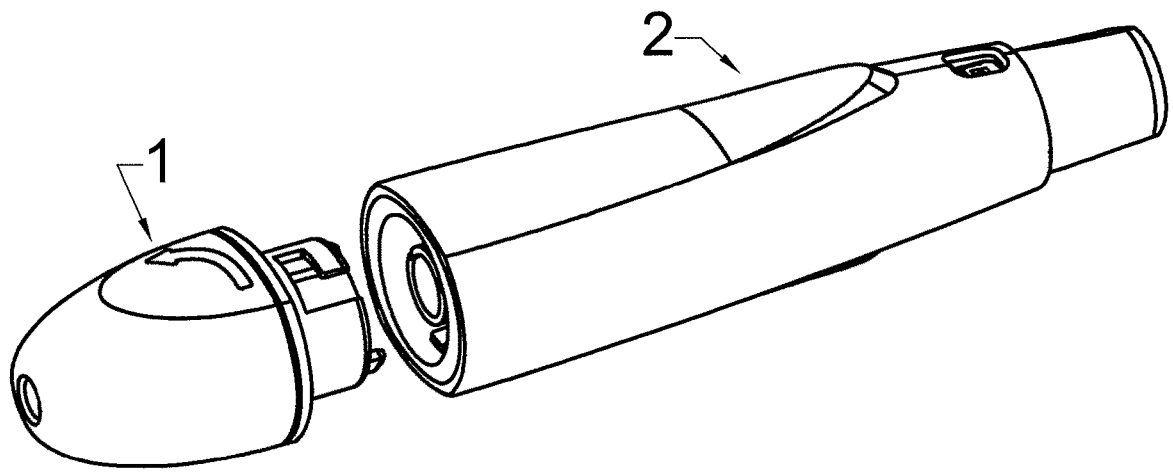
Figure 6:
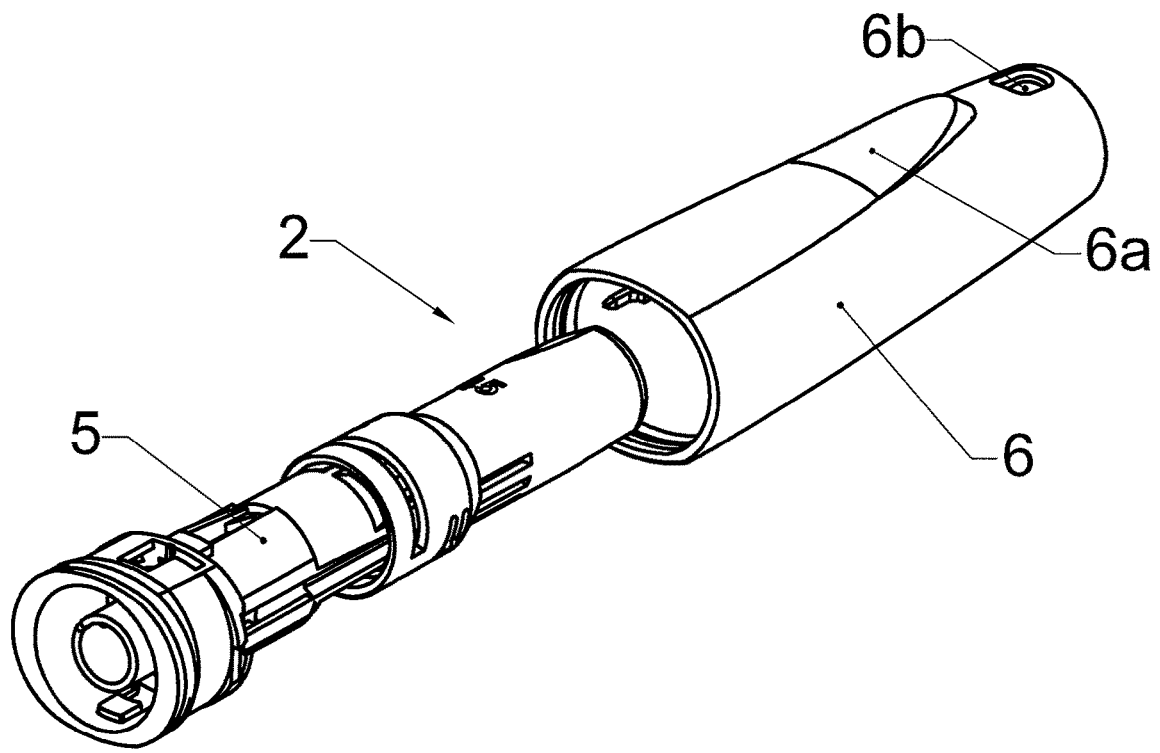
Figure 7:
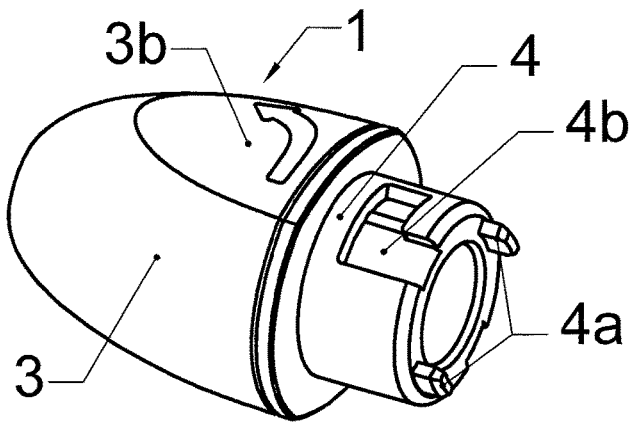
Figure 8:
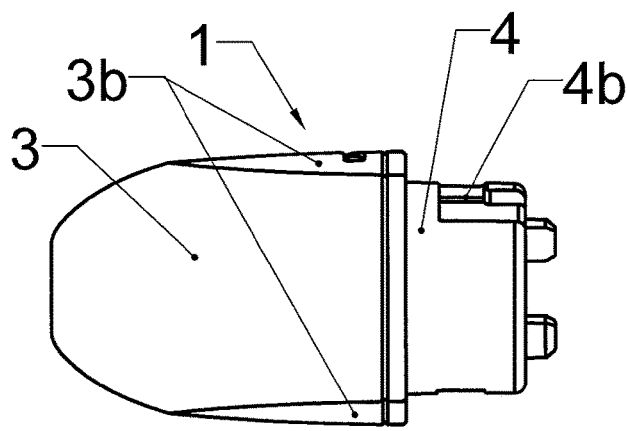
Figure 9:
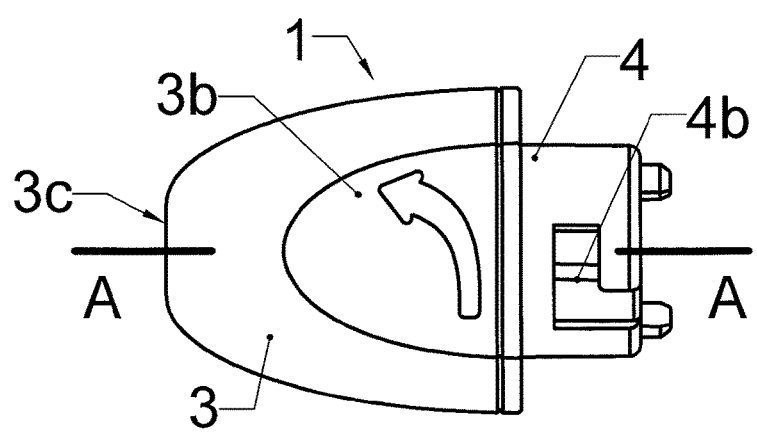
Figure 10:
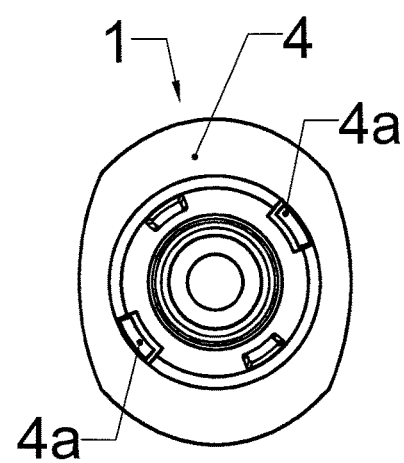
Figure 11:
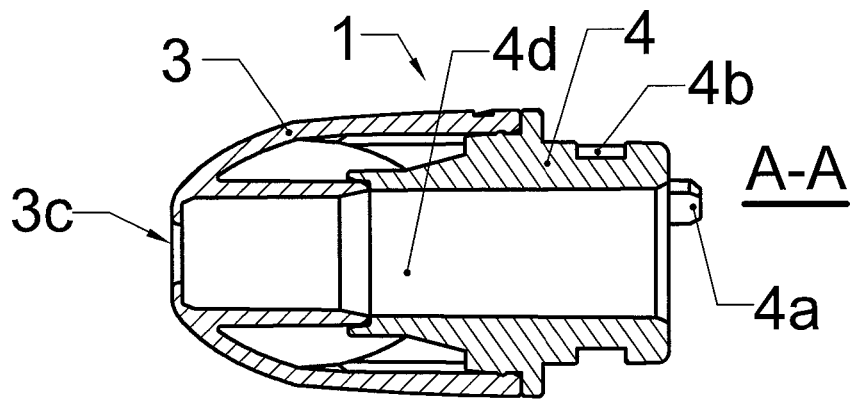
Figure 12:
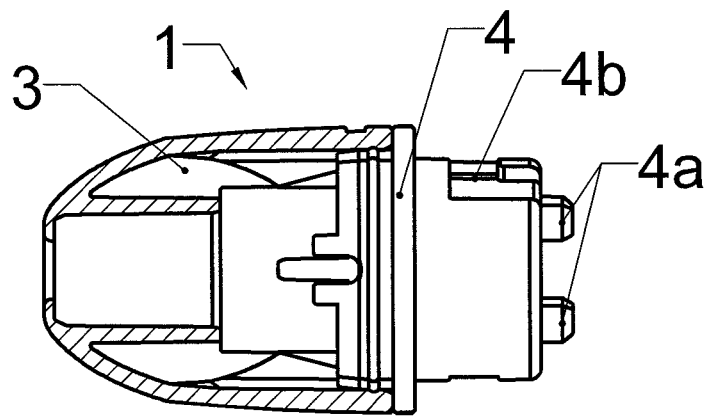
Figure 13:
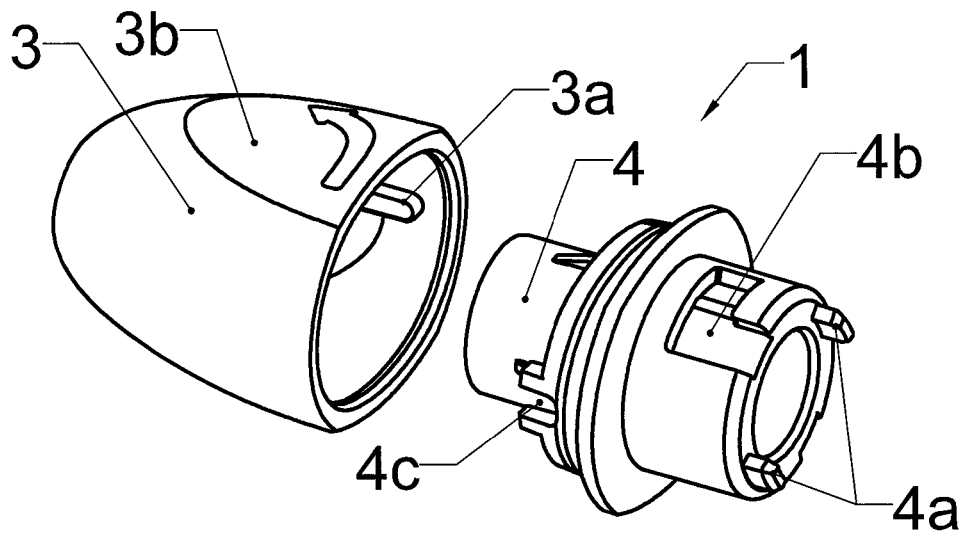
Figure 14:
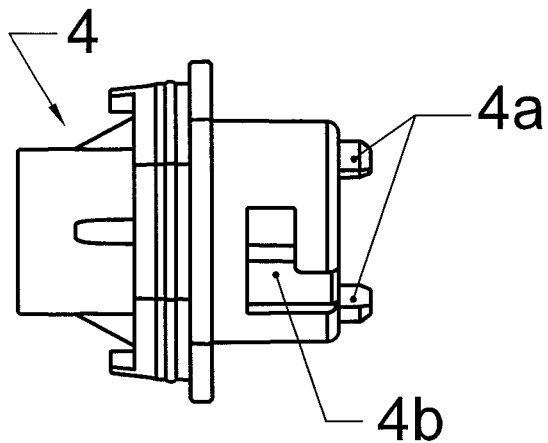
Figure 15:
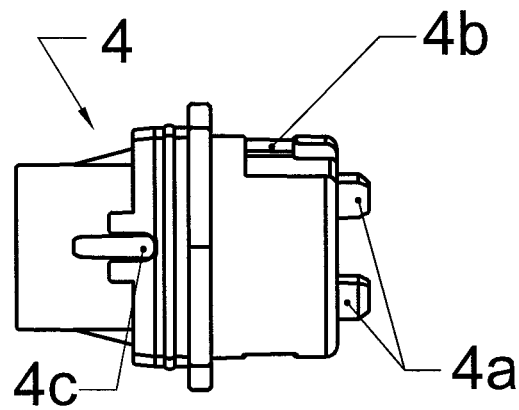
Figure 16:
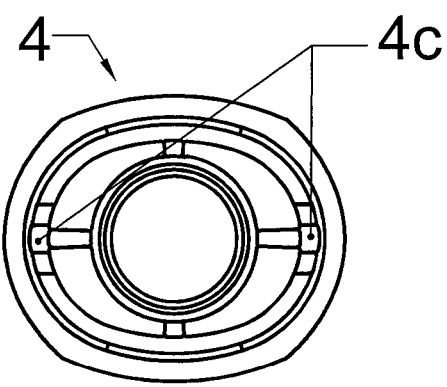
Figure 17:
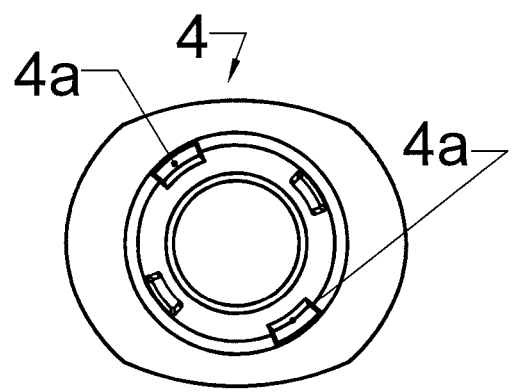
Figure 18:
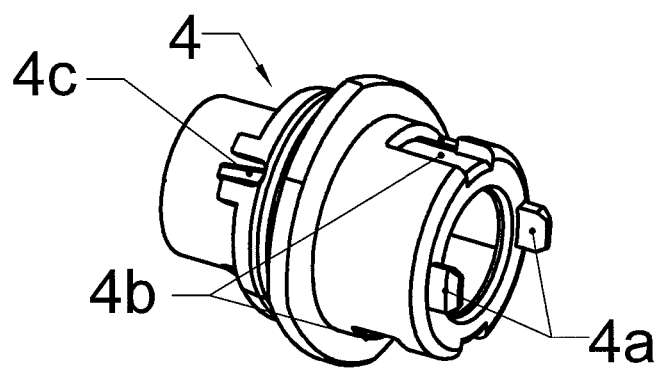
Figure 19:
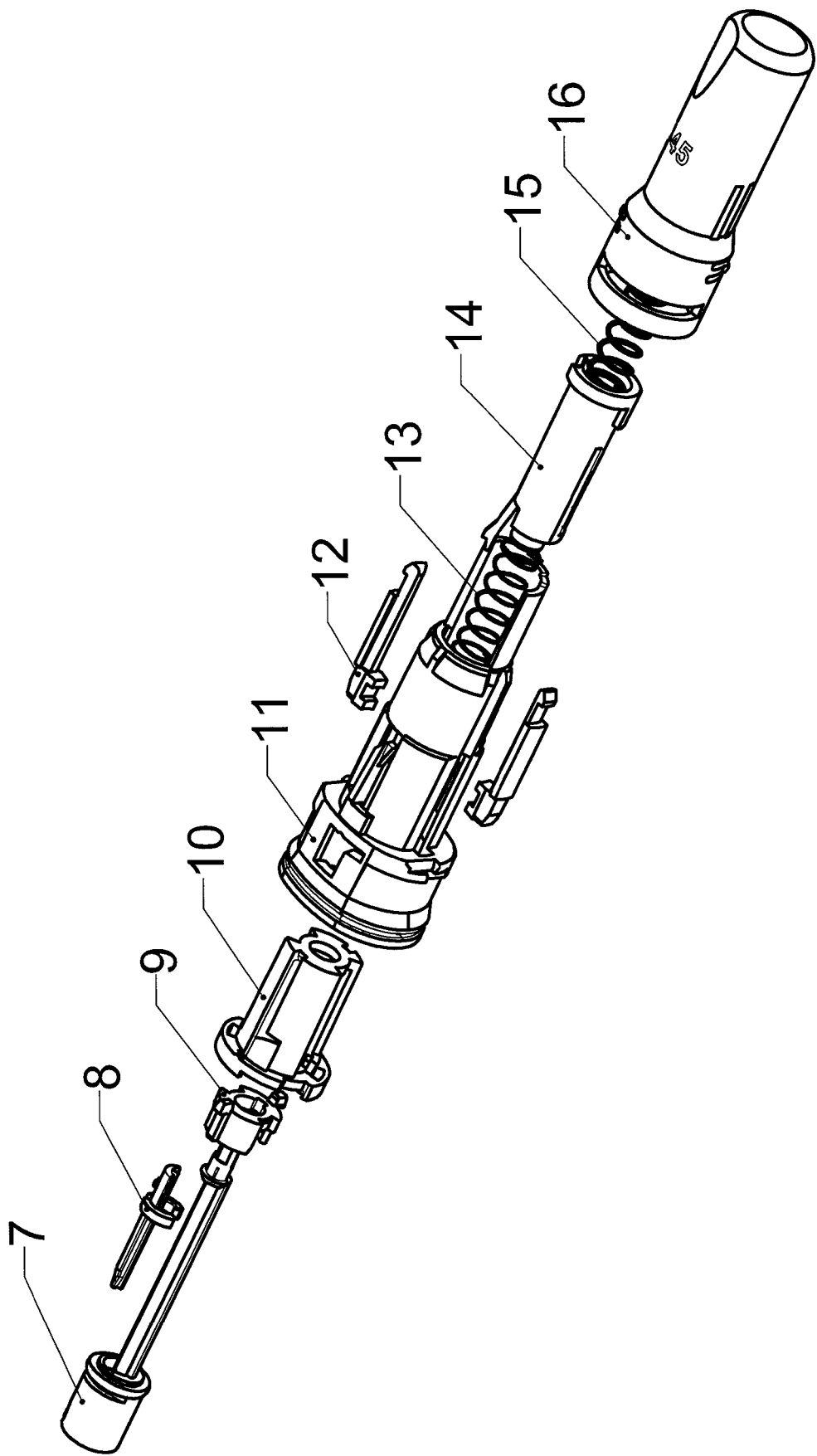
Figure 20:
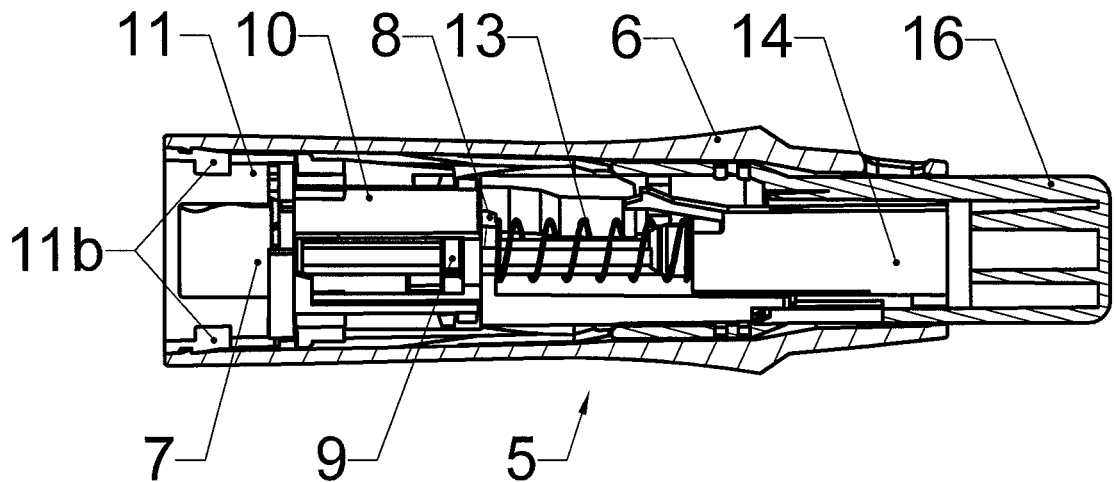
Figure 21:
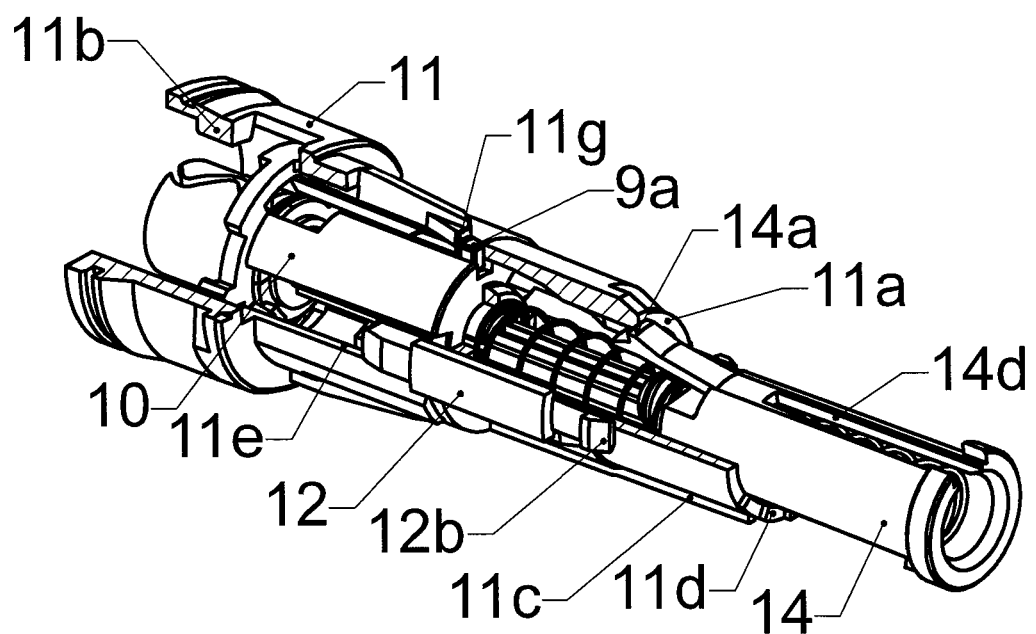
Figure 28:
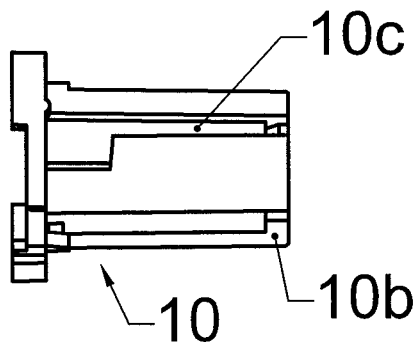
Figure 30:
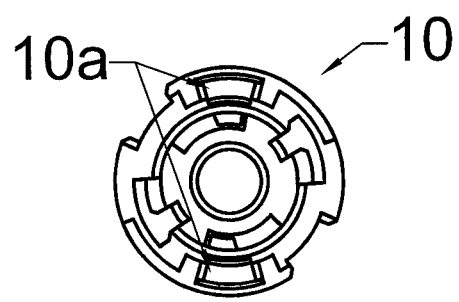
Figure 29:
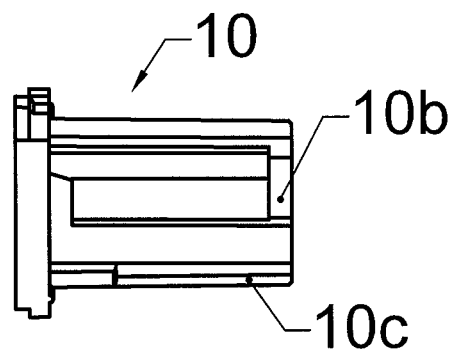
Figure 31:
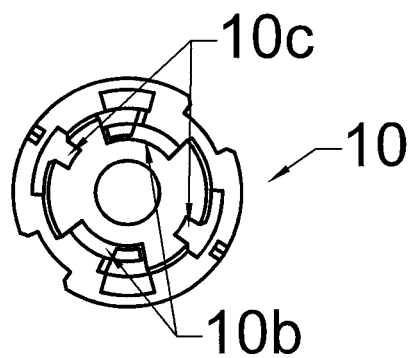
Figure 32:
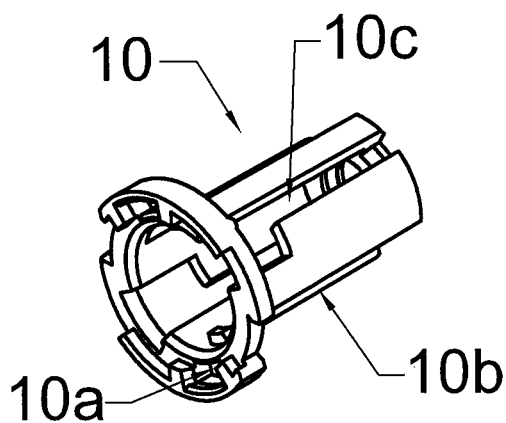
Figure 33:
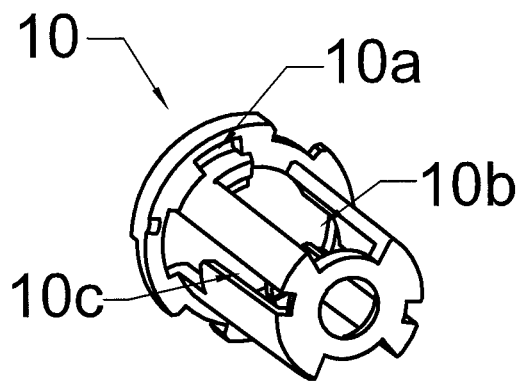
Figure 34:
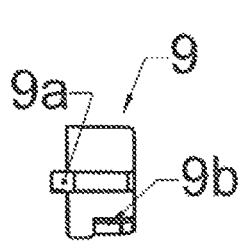
Figure 35:
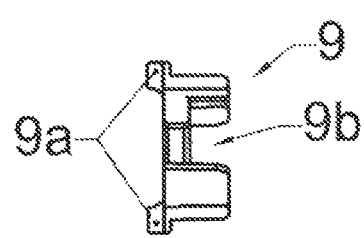
Figure 36:
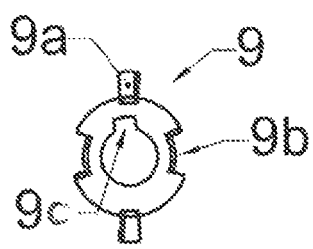
Figure 37:
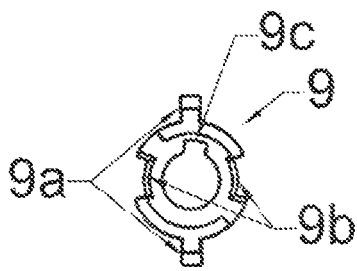
Figure 38:
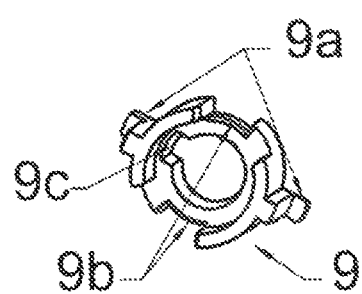
Figure 39:
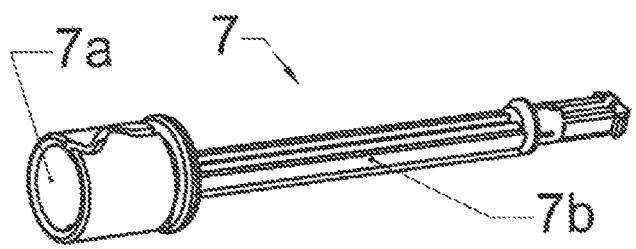
Figure 40:
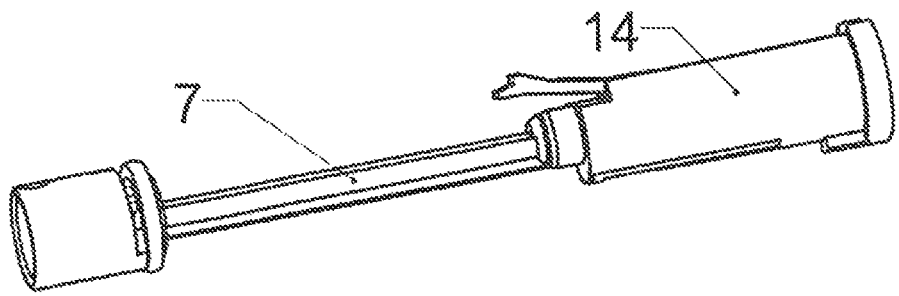
Figure 42:
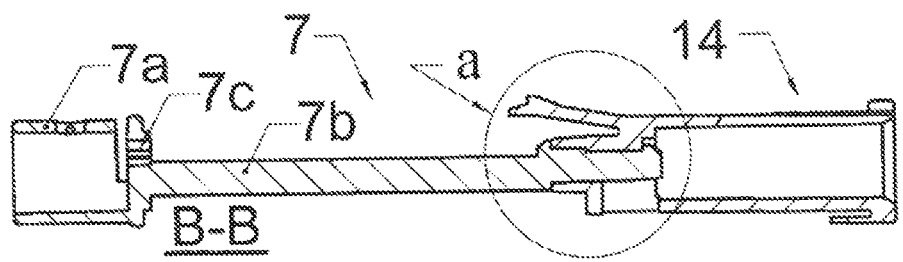
Figure 41:
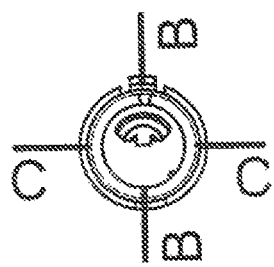
Figure 44:
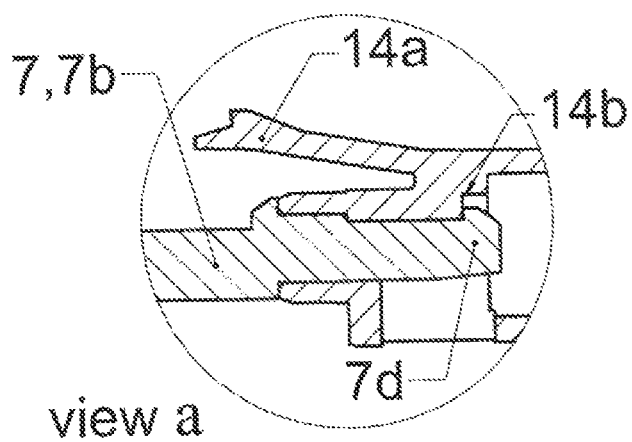
Figure 43:
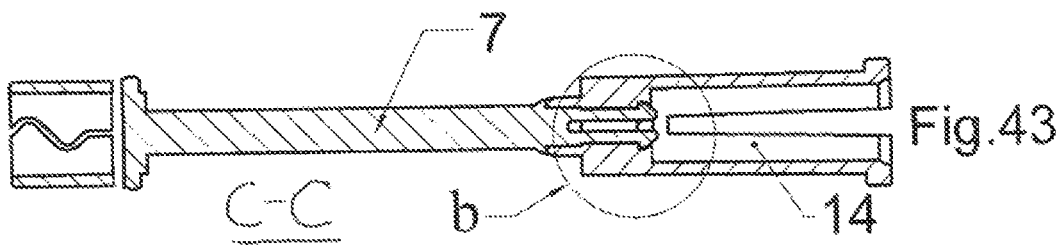
Figure 45:
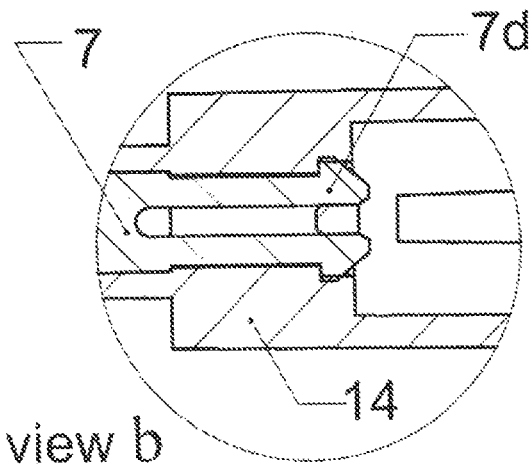
Figure 46:
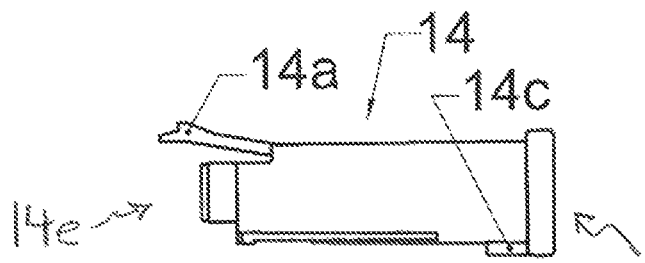
Figure 47:
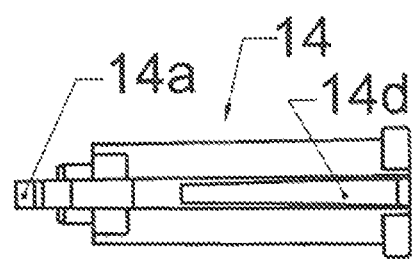
Figure 48:
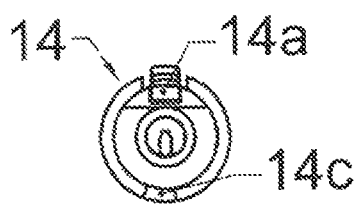
Figure 49:
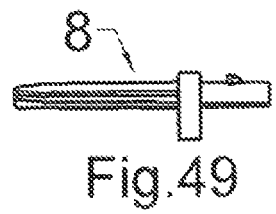
Figure 50:
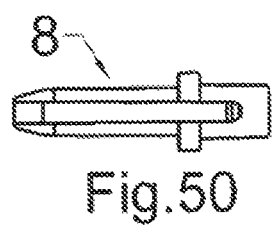
Figure 51:
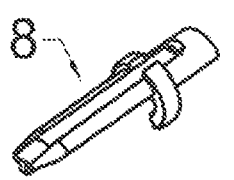
Figure 52:
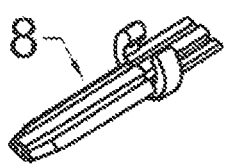
Figure 53:
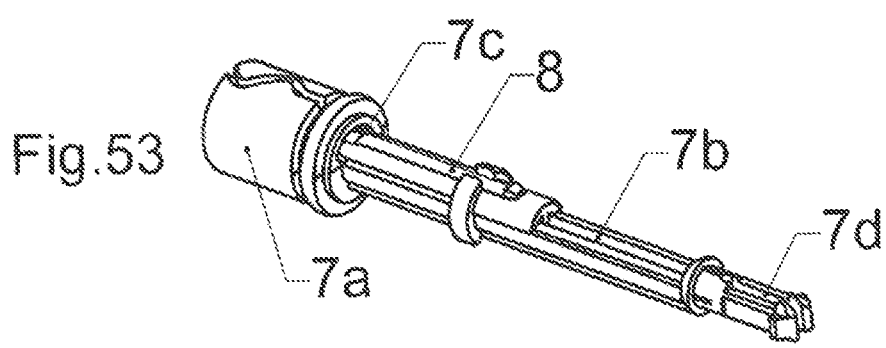
Figure 54:
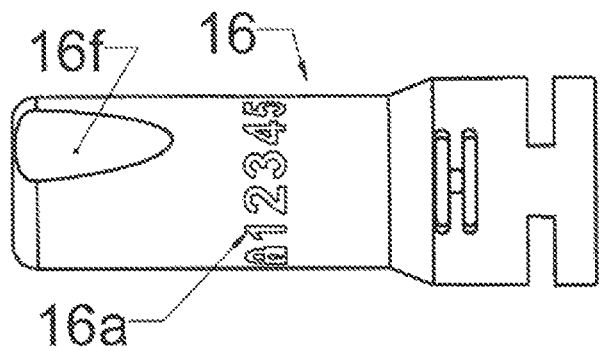
Figure 55:
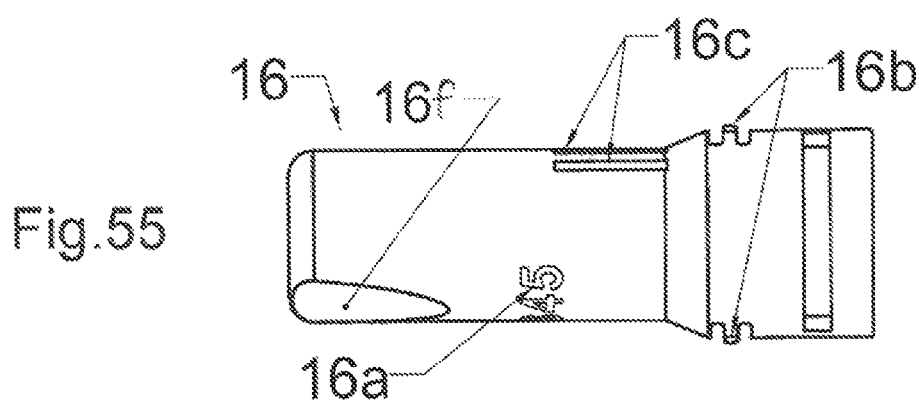
Figure 56:
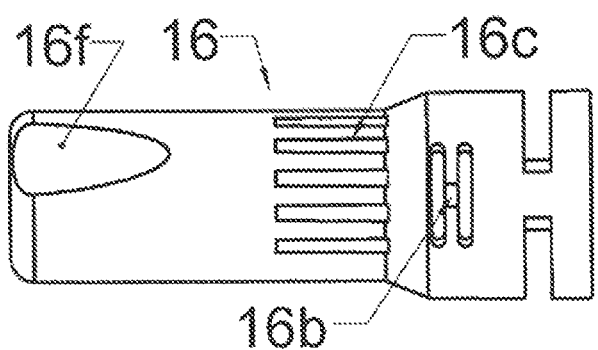
Figure 57:
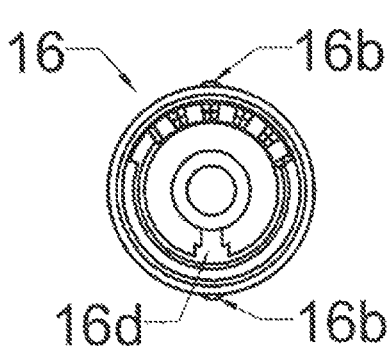
Figure 58:
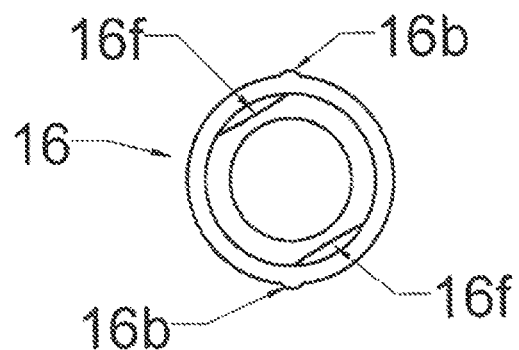
Figure 59:
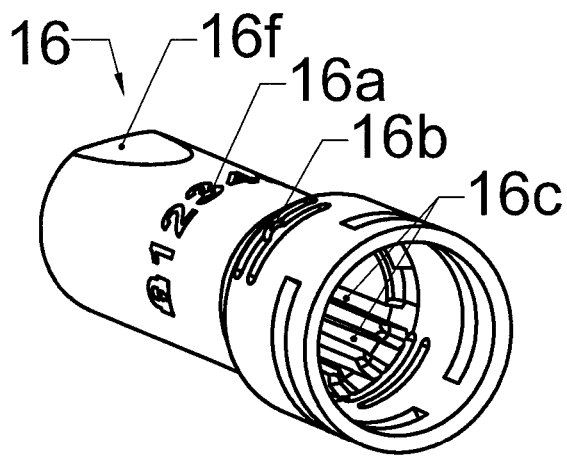
Figure 60:
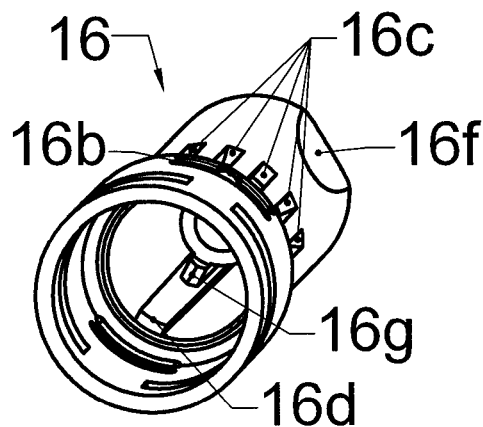
Figure 61:
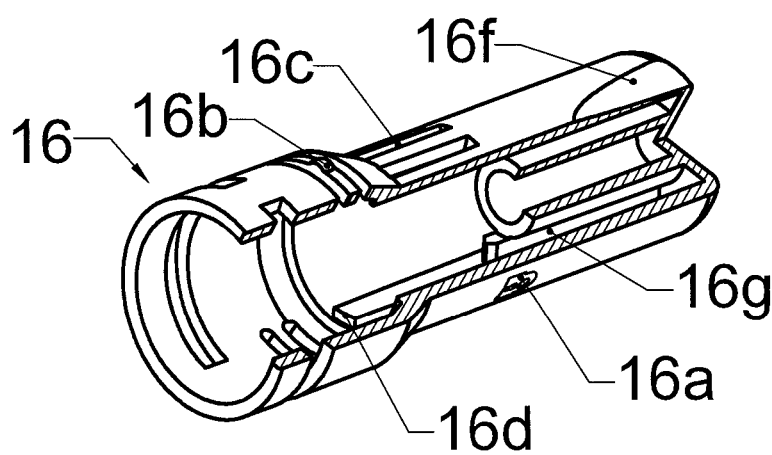
Figure 62:
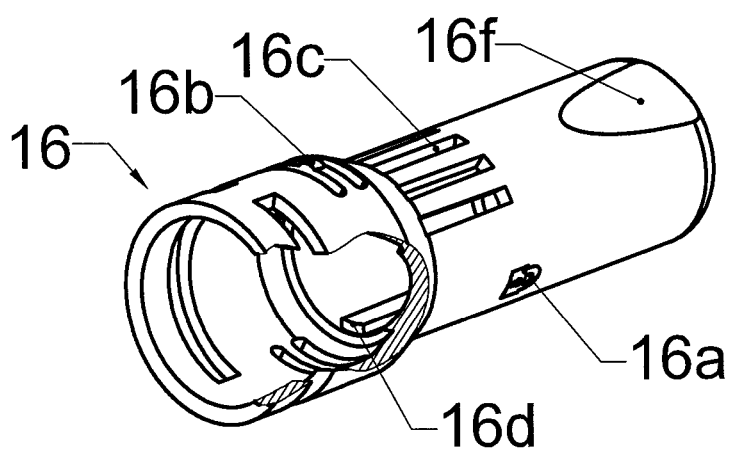
Figure 63:
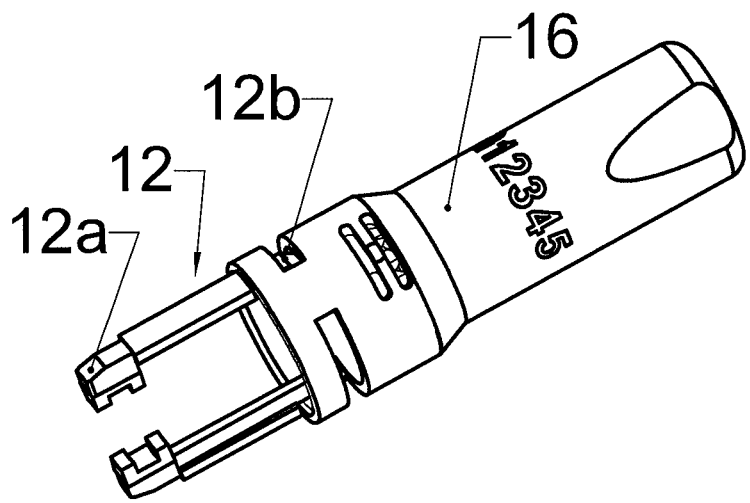
Figure 64:
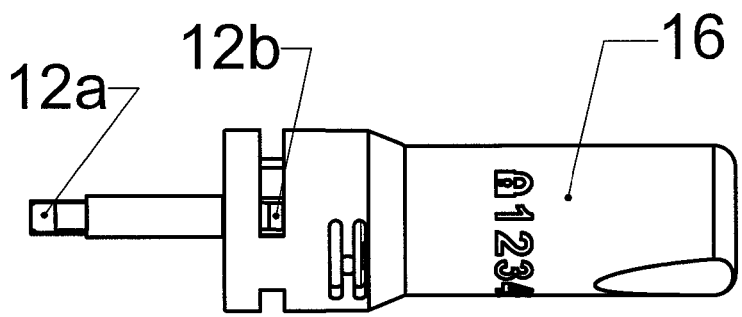
Figure 65:
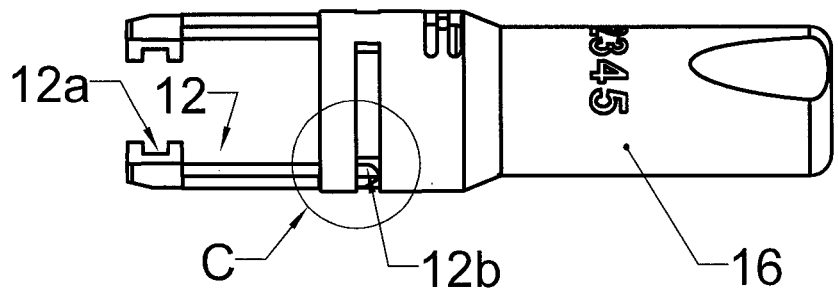
Figure 66:
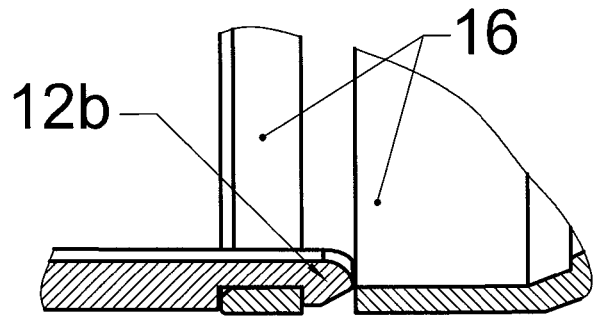
Figure 67:
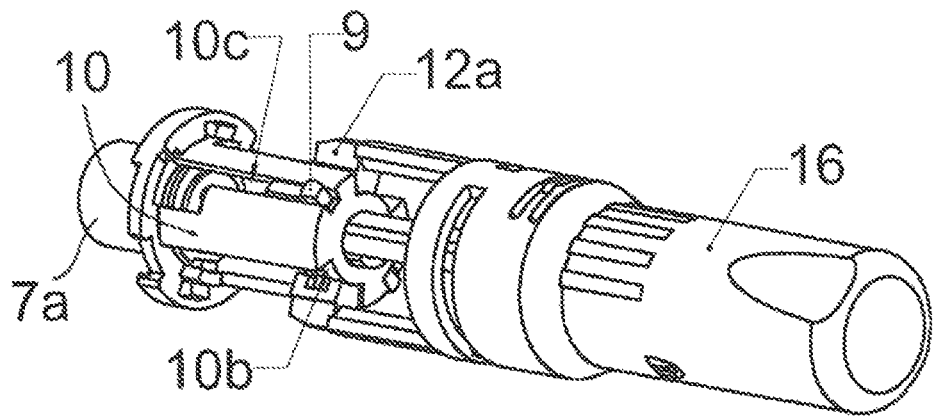
Figure 68:
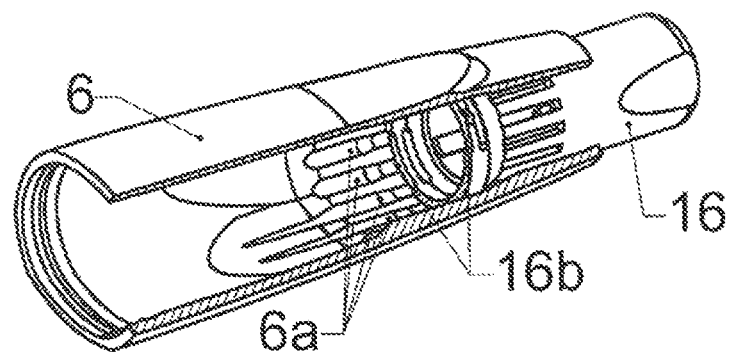
Figure 69:
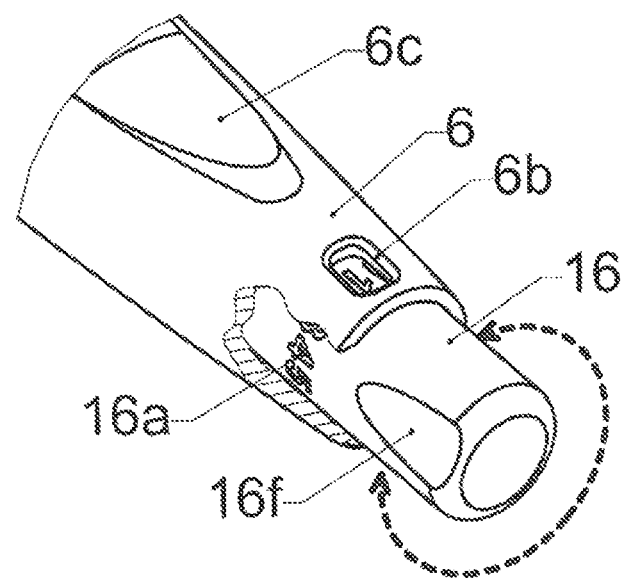
Figure 70:
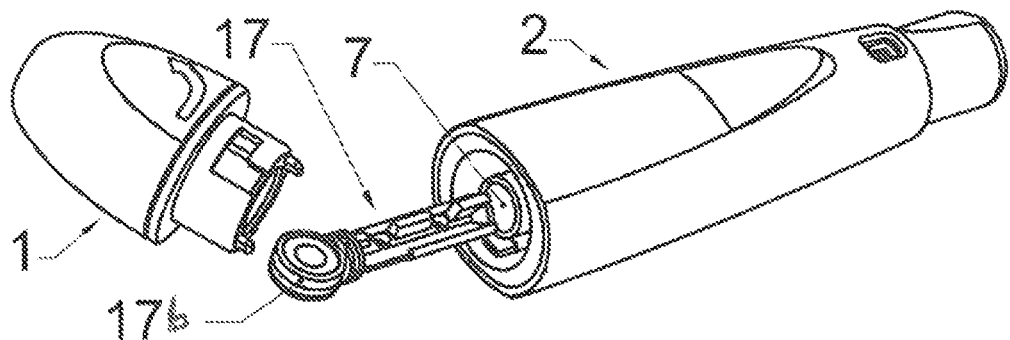
Figure 71:
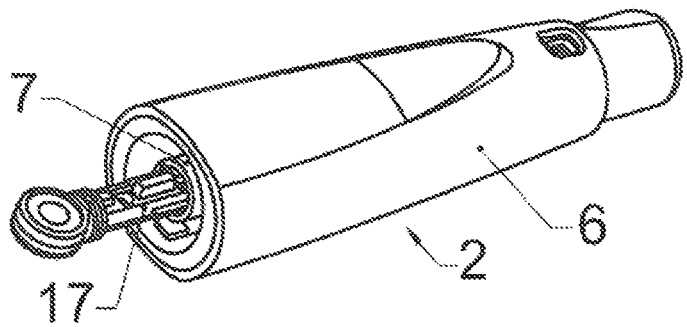
Figure 72:
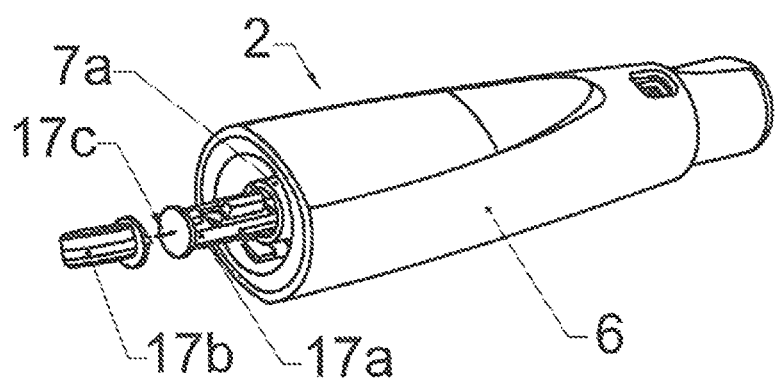
Figure 73:
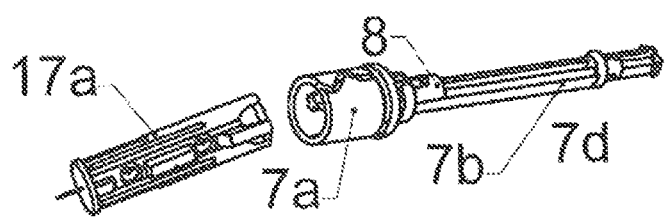

The invention, shown in the figures of the drawings as exemplary embodiments, but scale between the figures is not kept. FIG. 1 and FIG. 2 present the device from the side and from the top, respectively. FIG. 3, FIG. 4, and FIG. 5 present axonometric views of the device with the cup assembled, rotated, and removed, respectively. FIG. 6 presents an axonometric view of the casing of the main body and the mechanism unit installed in the casing. FIG. 7 presents the axonometric view of the cup of the device. FIG. 8, FIG. 9, and FIG. 10 present the cup from the side, from the top, and from the back, respectively. FIG. 11 presents a longitudinal section of the cup presented in FIG. 8, while FIG. 12 presents a longitudinal section of the same cup sheath. FIG. 13 presents the components of the cup from FIG. 7, that is its sheath and base. FIG. 14 and FIG. 15 present the base of the cap from the top and from the side, respectively. FIG. 16, FIG. 17, and FIG. 18 present the cap from the front, from the back, and in axonometric view, respectively. FIG. 19 presents a so-called exploded-view drawing of the mechanism unit, FIG. 20 presents the longitudinal section of the main body, and FIG. 21 presents an axonometric view of the assembled mechanism unit from FIG. 19, with removed button and in partial cross-section. FIG. 22, FIG. 23, FIG. 24, and FIG. 25 present the mechanism body from below, from the side, from the front, and from the back, respectively. FIG. 26 presents the axonometric view of the mechanism body with partial cross-section, while FIG. 27 presents another axonometric view of the mechanism body. FIG. 28 and FIG. 29 present the setting of a driver in two separate views from the sides, FIG. 30 and FIG. 31 present the same setting from the front and from the back, respectively, FIG. 32 and FIG. 33 present the setting in axonometric views from the front and from the back, respectively. FIG. 34 and FIG. 35 present the driver in two different views from the sides, while FIG. 36 and FIG. 37 present the driver from the back and from the front, respectively, FIG. 38 presents the driver in axonometric view. FIG. 39 presents the axonometric view of the lancet socket, while FIG. 40 presents the axonometric view of the lancet socket linked with the driving sleeve. FIG. 41 presents the lancet socket from the front, with two cut surfaces, FIG. 42 presents the cross-section of the unit of FIG. 40 in cross-section, using one of the planes of FIG. 41, and FIG. 43 presents the cross-section of the same unit, using the second plane of FIG. 41. FIG. 44 presents an enlarged fragment of the cross-section shown in FIG. 42 and FIG. 45 presents an enlarged fragment of the cross-section shown in FIG. 43. FIG. 46, FIG. 47, and FIG. 48 present the driver sleeve shown in FIG. 40 from the side, from below, and from the front, respectively. FIG. 49 presents a lancet ejector from the side and FIG. 50 presents the same lancet ejector from the top. FIG. 51 and FIG. 52 present the ejector in axonometric views from the top and from below, respectively. FIG. 53 presents lancet socket with ejector fitted. FIG. 54, FIG. 55, and FIG. 56 present the button from the three separate side views, FIG. 57 presents the same button from the front, and FIG. 58 presents the button from the back. FIG. 59 and FIG. 60 present two different axonometric views of the button, while FIG. 61 and FIG. 62 present another axonometric view of the button with two different partial cross-sections. FIG. 63 presents the button with two mounted side sliders in axonometric view, while FIG. 64 and FIG. 65 present the same button with side sliders in two different views from the sides. FIG. 66 presents the cross-section of a magnified detail of mounting the side slider to the button from FIG. 65. FIG. 67 presents the mechanism unit in axonometric view, without the casing. FIG. 68 and FIG. 69 present in two axonometric views partial cross-sections of the main body with assembled button. FIG. 70, FIG. 71, and FIG. 72 present three subsequent phases of installing the lancet in the puncturing device, while FIG. 73 presents the same lancet socket with a used lancet, removed by the ejector. Figures from FIG. 74 to FIG. 96 present six subsequent phases, described below, of the functioning of the device during performing the puncture. FIG. 74, FIG. 75, FIG. 76, FIG. 77, and FIG. 78 present the cross-sections of the device during the first phase. FIG. 79, FIG. 80, FIG. 81, and FIG. 82 present the cross-sections of the device during the second phase. FIG. 83, FIG. 84, FIG. 85, and FIG. 86 present the cross-sections of the device during the third phase. FIG. 87, FIG. 88, FIG. 89, and FIG. 90 present the cross-sections of the device during the fourth phase. FIG. 91, FIG. 92, FIG. 93, and FIG. 94 present the cross-sections of the device during the fifth phase. FIG. 95 and FIG. 96 present the cross-sections of the device during the sixth phase of its activity.

Below you will find a detailed description of the exemplary embodiment of the invention. The puncturing device is composed of the main body 2 and the cup 1, mounted separatable on the main body 2. The end of the device with the cup 1 is its front end; therefore, the opposite end is the back end of the device. The top of the device is where the window in the body for the symbols for the puncture depth is located, described in the further part. The cup 1 is composed of the cup sheath 3 and the permanently attached inside it cup base 4. The main body 2 is composed of the mechanism unit 5, located in the casing 6. The mechanism unit 5 includes the lancet socket 7, ejector 8, driver 9, driver setting 10, mechanism body 11, return spring 13, and driving sleeve 14. The mechanism body 11 is fixed in place by its shape in casing 6. The driving sleeve 14 is covered by button 16, linked with two side sliders 12, which slide in the side channel 11e of the mechanism body 11. The front latches 12a of the side sliders 12 reach inside the mechanism body 11 and cooperate with the driver 9. Between the driving sleeve 14 and button 16, there is the drive spring 15. Lancet socket 7 has lancet chamber 7a for lancet 17 and oblong guide 7b. The lancet chamber 7a is run in channel 4d of the cup base 4 of the cup 1. On the free end of the guide 7b, the driving sleeve 14 is fixed on with latches 7d. The ejector 8 is fitted sliding on the guide 7b. The setting of driver setting 10 is fitted rotating inside the mechanism body 11. The driver 9 is fitted sliding inside the driver setting 10. The said guide 7b of the lancet socket 7 protrudes through the driver 9, driver setting 10, through transverse partition 11f of the mechanism body 11, and return spring 13. Cup 1 is assembled to the main body 2 with a bayonet connector, which consists of notches 4b in the cup base 4 and corresponding projections 11b in the front part of the mechanism body 11. After removing the cup 1, a disposable lancet 17 is installed by pushing it into the lancet chamber 7a of the lancet socket 7, deep inside the lancet chamber 7a, until noticeable resistance is felt. In such state the puncturing device is blocked, so is impossible for the lancet socket 7 to either retract inside of the casing 6 or to puncture with the lancet 17 assembled in the lancet socket 7. After installing the lancet 17 in the lancet socket 7, the blade cover 17*b* is twisted off and removed, thus uncovering the metal puncturing lancet blade 17*c*, so in other words the lancet 17 safety is removed. In the described embodiment, the widely known and commonly used lancet 17 is applied, in which the metallic needle is embedded in a plastic fitting with blade cover 17*b* on the sharp end of the needle, divided from the main part of the fitting with a necking. In order to remove the blade cover 17*b*, it must be twisted off around the lancet axis, which leads to breaking of the plastic in said necking and then removing it from the lancet blade 17*c* it covered. In order to install the mechanism unit 5 from the front into the mechanism body 11, the driver setting 10 is inserted and then the driver 9 is slid inside it. Then the ejector 8 is mounted on the guide 7*b* of the lancet socket 7, and then the guide 7*b* of the lancet socket 7 with the ejector 8 is put through in the central opening of the driver 9. The return spring 13 is placed on the end of the guide 7*b* protruding from the end part of the mechanism body 11, then rested on the traverse partition 11*f* of the mechanism body 11, and then the driving sleeve 14 is inserted into the mechanism body 11 from the back. By overcoming the resistance of the return spring 13 and the latches 7*d* of the guide 7*b*, the driving sleeve 14 is locked on the back part of the guide 7*b* of the lancet socket 7. Then the side sliders 12 are inserted in the side channels 11*e* of the mechanism body 11 and moved toward the back of the mechanism body 11 to their maximum position. The drive spring 15 is inserted into the driving sleeve 14 and then the driving sleeve 14 with the drive spring 15 is covered by the notched button 16. The front part of the button 16 catches on the back latches 12*b* of the side sliders 12. Such assembled mechanism unit 5 is inserted from the front into the casing 6 until a circumferential projection of the casing 6 clicks in a circumferential groove on the front end of the mechanism body 11. When assembled, part of the button 16 with finger notches 16*f*, which makes it easier to rotate the button 16 against the casing 6, protrudes from the main body 2. Fitting the cup 1 to the main body 2 is done by inserting the cup 1 deep inside the main body 2, taking care to aim the two notches 4*b* of the cup 1 onto the two projections 11*b* inside the mechanism body 11. After pushing the cup 1 into the front surface of the main body 2, the cup 1 is twisted clockwise until a recognizable click and definite resistance. In order to facilitate twisting the cup 1 against the main body 2, the cup sheath 3 of the cup 1 has two notches 3*b*, which make gripping the cup 1 with fingers easier, while the casing 6 has elevated shape 6*c*, easy to grip. Unintended twisting of the cup sheath 3 against cup base 4 is prevented by the interlock of the components, that is the projections 3*a* inside the cup sheath 3, which go into the notches 4*c* in the cup base 4.

The puncturing device has puncture depth step regulation function—i.e., possibility to change the distance the lancet blade 17*c*, is shot out of the front surface 3*c* of the cup sheath 3. Choosing the depth is done by rotating button 16 in angles ranging from 0to 120°, in which the button 16 locks clearly and audibly with a click in one of the six positions. The first of these positions, in the described exemplary embodiment is indicated on the button 16 with a padlock symbol. This position is so-called locked position, in which pressing the button 16 is not possible and this position secures the device from unintended activation. The set depth is indicated by the symbols 16*a* on the button 16, visible through a window 6*b* in the casing 6 (FIG. 69). In the described exemplary embodiment these symbols are numbers from 1 to 5. The stepped rotation of the button 16 is the result of two projections 16*b*, located on the opposite sides of the button 16 and being its integral parts, locking in twelve relevant locking channels 6*a* on the inner surface of the casing 6 (FIG. 68).

Figure 74:
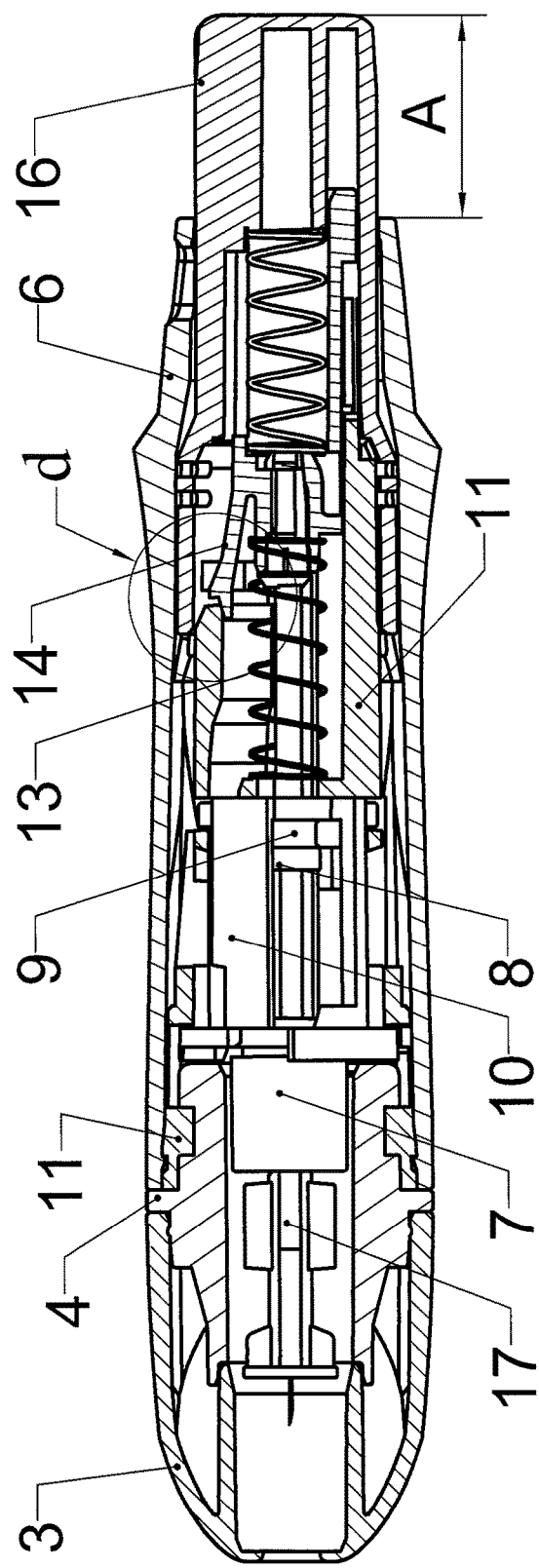
Figure 75:
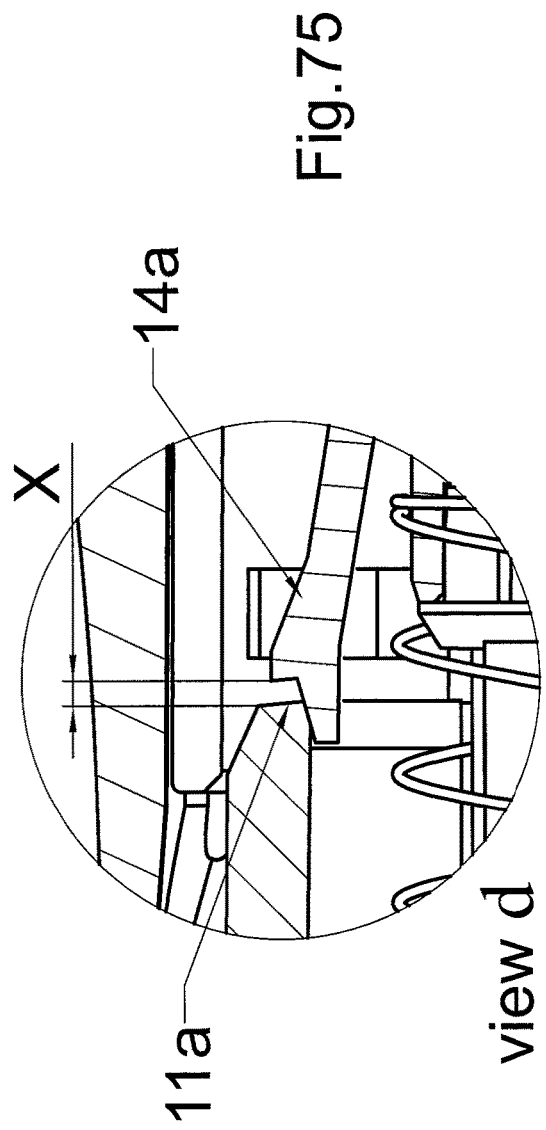
Figure 76:
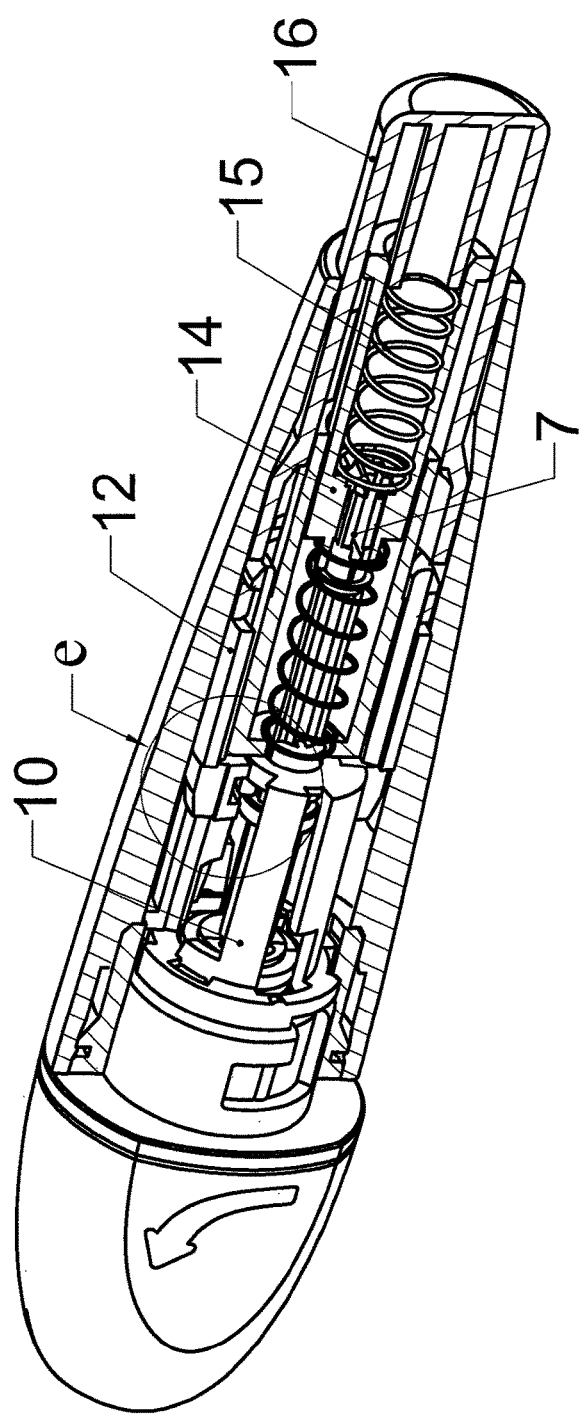
Figure 78:
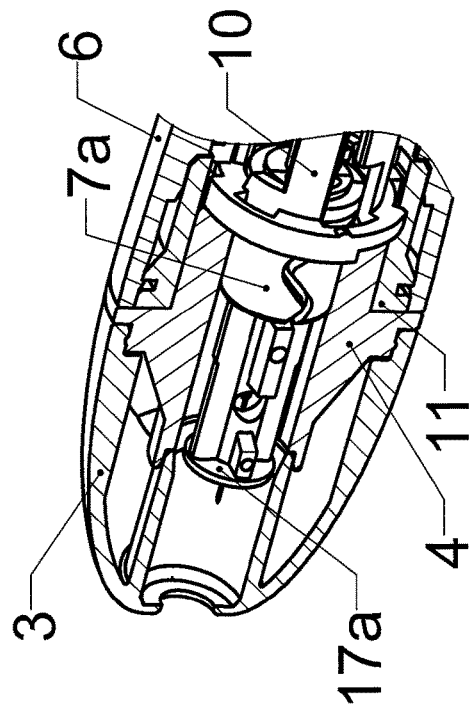
Figure 77:
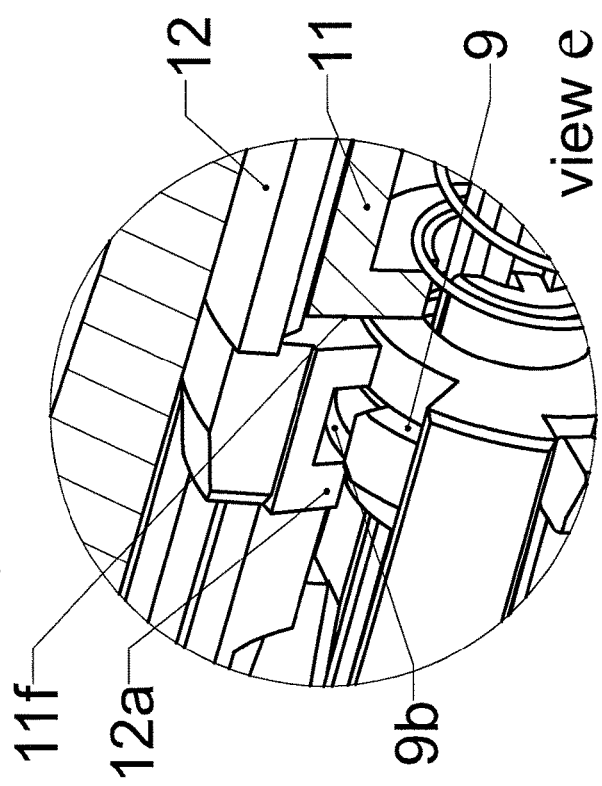
Figure 81:
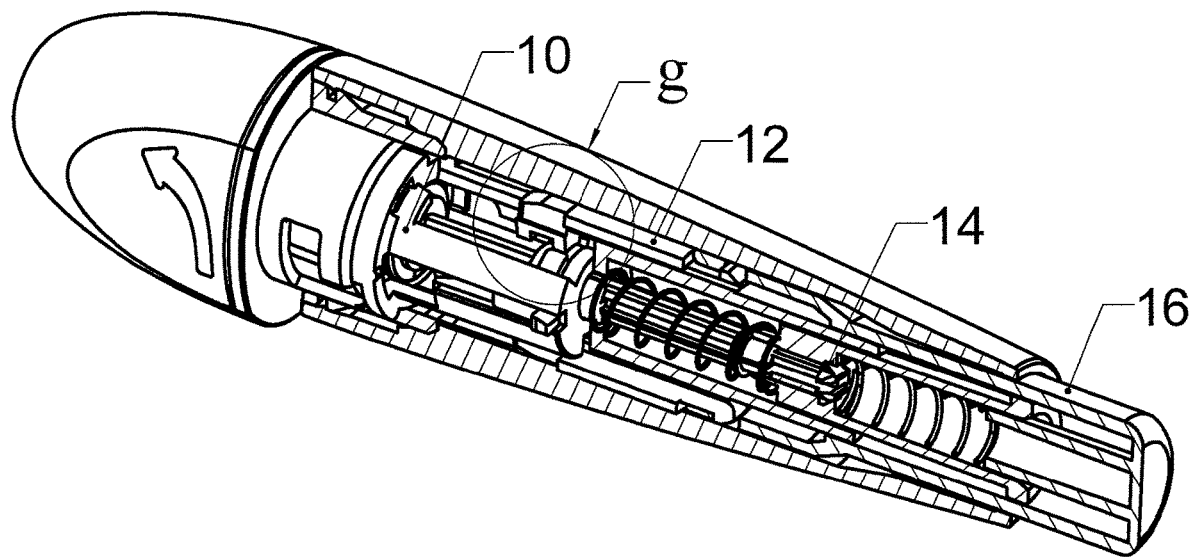
Figure 82:
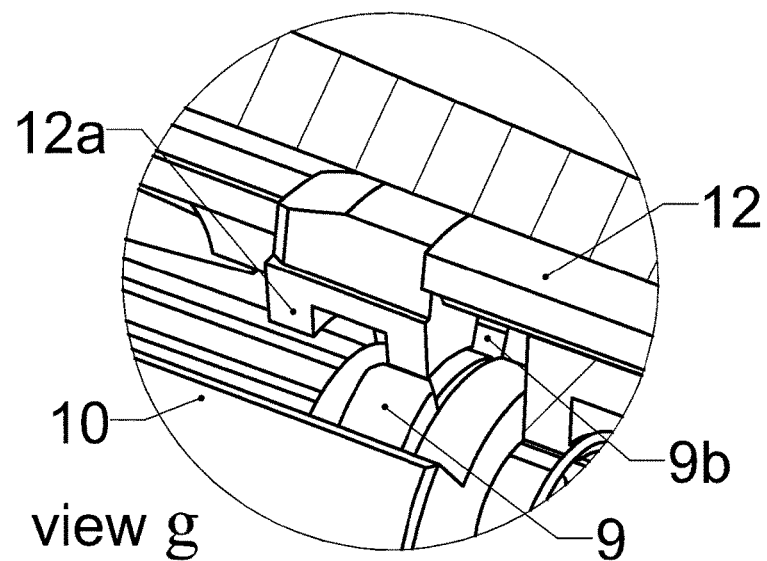
Figure 83:
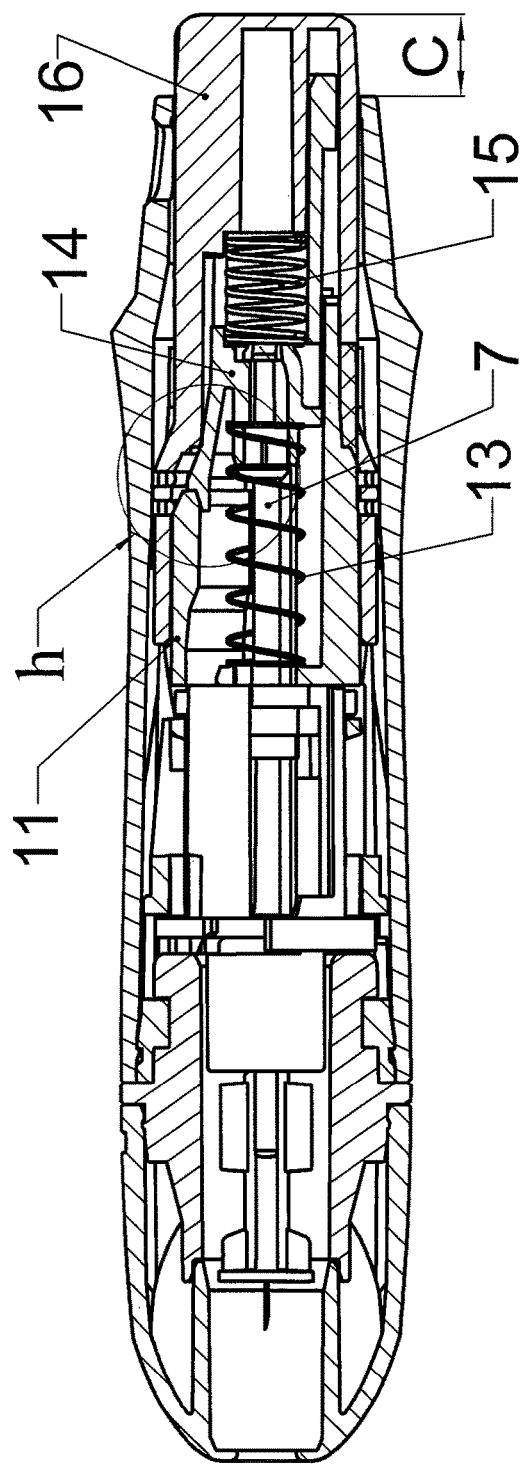

The FIG. 74 presents the cross-section of the puncturing device in the first phase that is the preparation for puncturing. In this phase, the button 16 protrudes maximally towards the back of the device by distance A, which in this exemplary embodiment amounts to ca. 14 mm. This protrusion is limited by two side sliders 12. In this phase the front latches 12*a* of the side sliders 12 rest on the front surface of the transversal partition 11*f* of the body 11 (FIG. 77). The button 16 protrudes maximally towards the back because of the drive spring 15 and the return spring 13. The return spring 13 is loaded initially and based on the transverse partition 11*f* of the mechanism body 11 with one end and the second end exerting pressure on the driving sleeve 14, causing it to be pushed out of the mechanism body 11 that is towards the back. The retracting driving sleeve 14 exerts pressure on the drive spring 15, which in turn exerts pressure on the inner surface of the button 16, pushing it out of the mechanism body 11. The driving sleeve 14 has a front latch 14*a*, which is situated at a distance X, amounting to ca. 0.5 mm behind the stop surface 11*a* of the mechanism body 11, a front end 14*e* and a back end 14*f* (see FIG. 46). The driver 9 is positioned at an angle in such a way that its movement along the axis of the device is impossible, because two projections 9*a* of the driver 9 are positioned directly ahead of the two latches 11*g* of the mechanism body 11, while the front latches 12*a* of the side sliders 12 are positioned inside the notches 9*b* in the driver 9 (FIG. 76 and FIG. 77), thus the sliders 12 are not coupled with the driver 9. Lancet 17*a* is placed in the lancet socket 7, which is in the back part of the cup 1 (FIG. 74 and FIG. 78). On the outer surface of the body 11, underneath there is a fin 11*c*, which can engage one of the anti-rotating channels 16*c*, which are situated on the inner surface of the button 16. The number of these channels corresponds with the number of angular positions, in which the button 16 can be set in order to choose the depth of the puncture. When the button 16 is in the locked position, the fin 11*c* is on the opposite uniform surface inside button 16 that is out of the anti-rotation channels 16*c* system, which blocks the button 16 from being pressed and therefore also prevents puncturing or pushing the lancet out. The button 16 is rotary coupled with the driving sleeve 14, because its inner axial projection 16*g* fits in the axial notch 14*d* in the sleeve 14. Therefore rotating the button 16 automatically rotates the sleeve 14.

In phase two (Figures from 79 to 82) the symbol 16*a* is visible in the window 6*b* of the casing 6, which indicates the chosen depth of the puncture set with the button 16 and the fin 11*c* is positioned next to one of the channels 16*c* of the button 16. In this phase the pressed button 16 protrudes from the casing 6 at the distance B (FIG. 79), smaller than distance A and in this exemplary embodiment amounting to ca. 12 mm. As a result, the drive spring 15 becomes slightly compressed. The pressure of the drive spring 15 exerted on the driving sleeve 14 makes the driving sleeve 14 move, together with the lancet socket 7 along the axis of the device, deeper into the mechanism body 11, until the latch 14*a* of the driving sleeve 14 rests on the stop surface 11*a* of the mechanism body 11 (FIG. 80), resulting in reduction of the distance X to zero. Moving the driving sleeve 14 also causes slight compression of the return spring 13. The side sliders 12, coupled with the button 16, move forward, partially protruding from the notches 9b of the driver 9 (FIG. 81 and FIG. 82), but the driver 9 stays in the same position as in phase one.

Figure 84:
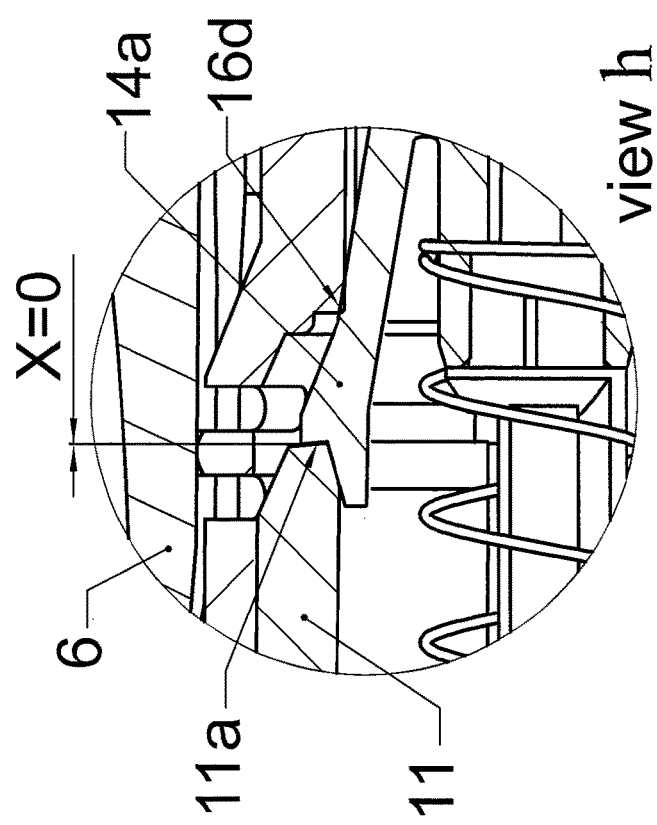
Figure 85:
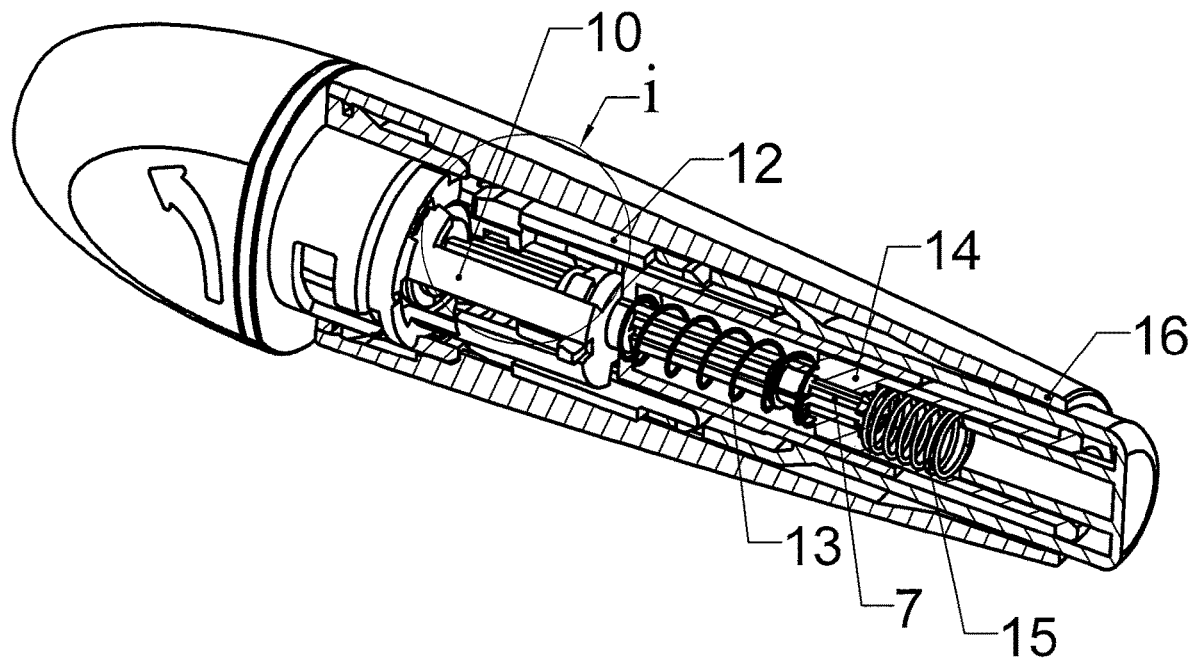
Figure 86:
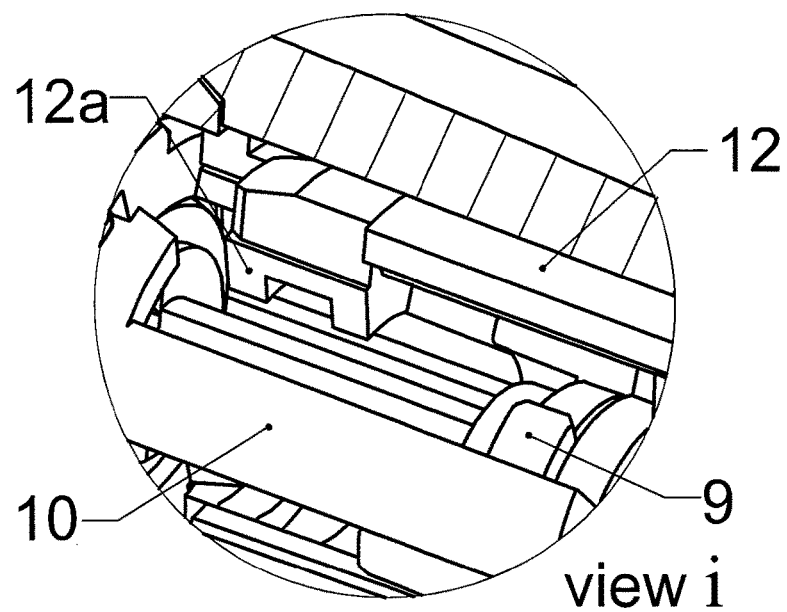
Figure 89:
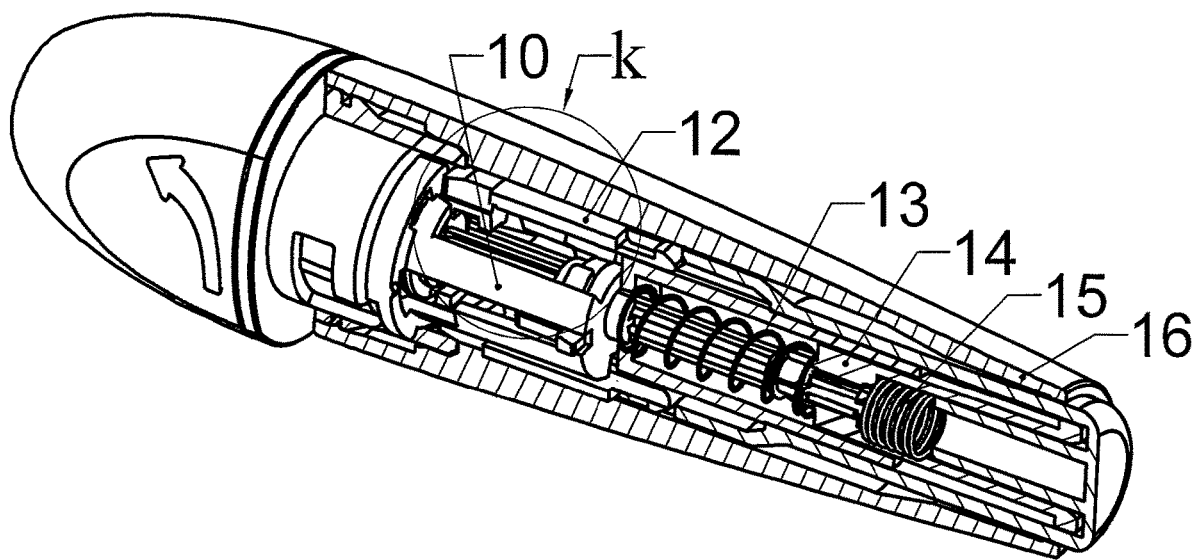
Figure 90:
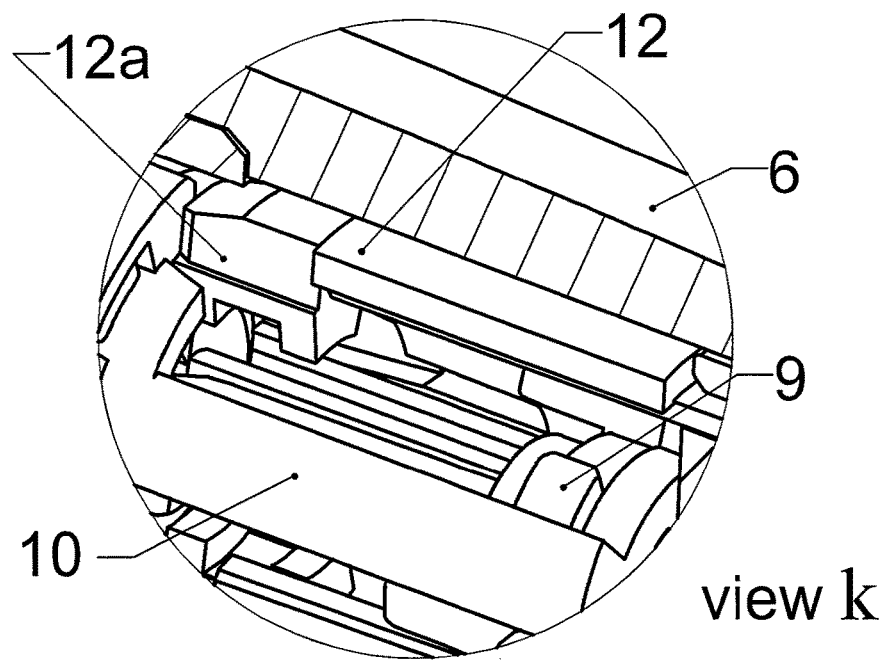
Figure 91:
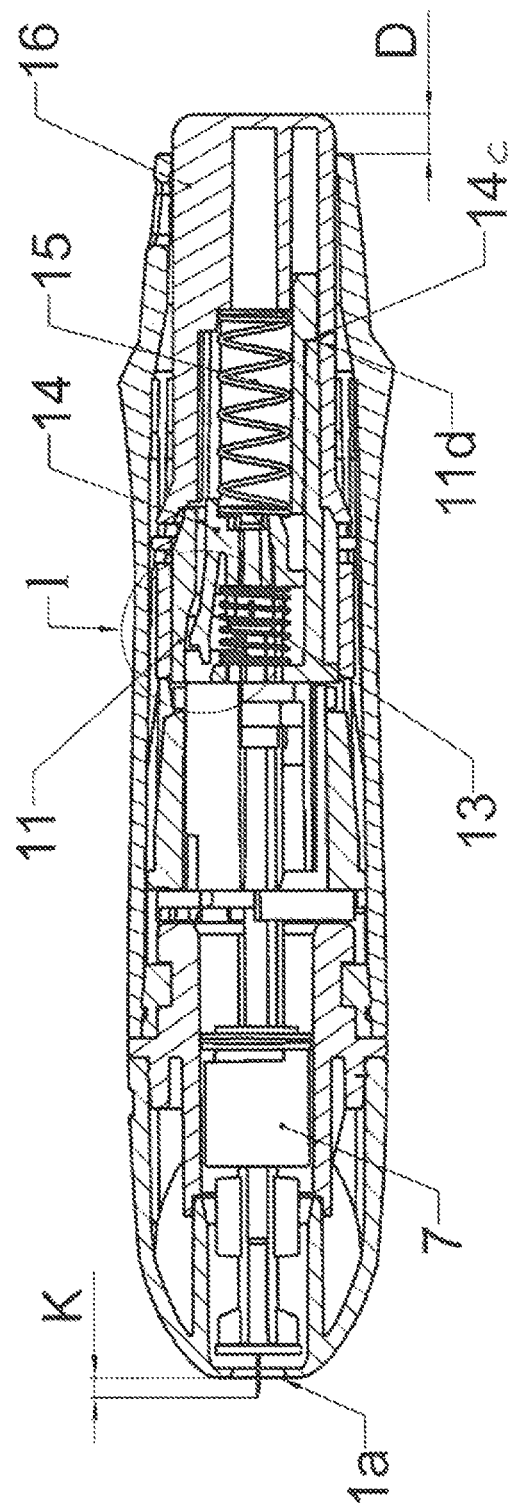
Figure 92:
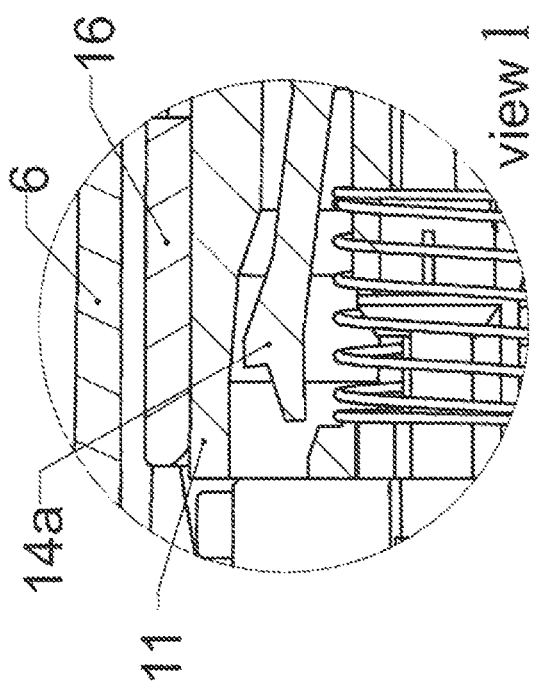

In third phase (Figures from 83 to 86) the button 16 is pushed even deeper, therefore it protrudes from the casing 6 by distance C (FIG. 83), which in this exemplary embodiment amounts to ca. 5.5 mm. Pushing the button deeper causes increasing the tension of the drive spring 15. The latch 14a of the driving sleeve 14 is still rested on the stop surface 11a of the mechanism body 11 (X=0, FIG. 84) and the tension of the return spring 13 does not change. The result of the movement of the button 16 is that the activating surface 16d touches the latch 14a of the driving sleeve 14 (FIG. 84). The side sliders 12, connected with the button 16, move towards the front of the device, coming out of the notches 9b of the driver 9 completely (FIG. 85 and FIG. 86). The driver 9 and driver setting 10 remain in the same position as in the first two phases.

In the fourth phase (Figures from 87 to 90) the button 16 is pressed till the end and rests on the body 11, but it protrudes from the casing 6 only by distance D (FIG. 87), which amounts in the exemplary embodiment to ca. 3 mm. The drive spring 15 is squeezed maximally and the activating surface 16d, pushing the latch 14a causes it to bend, to the position below the edge of the stop surface 11a (FIG. 88) and thus activating of the device.

Figure 93:
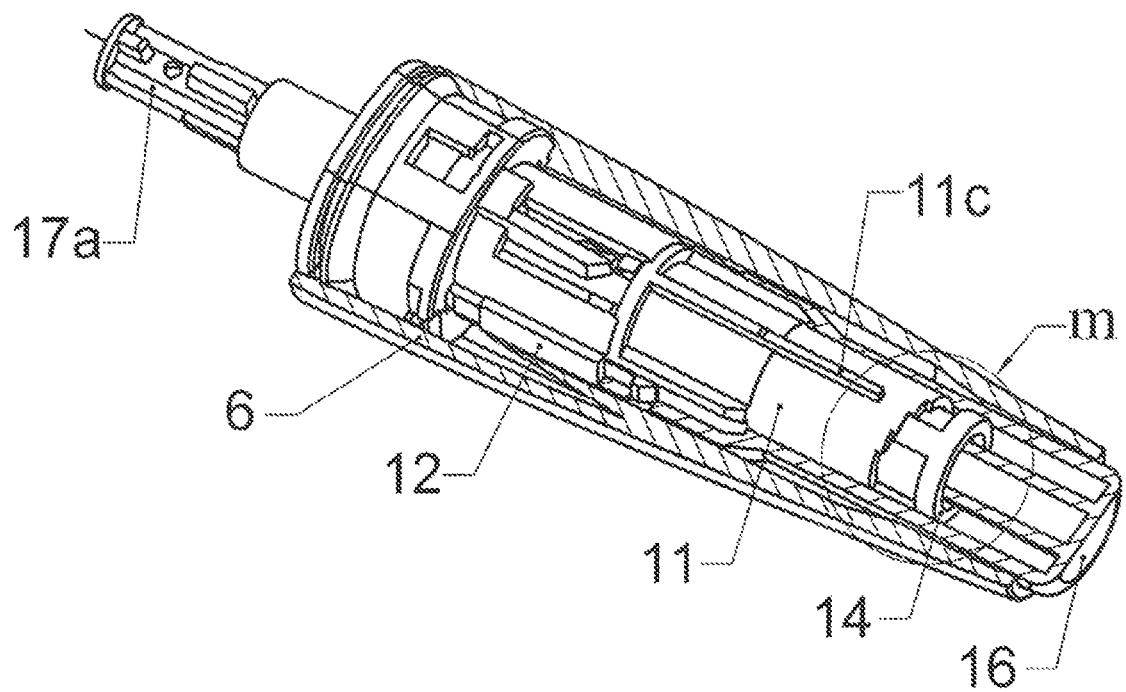
Figure 94:
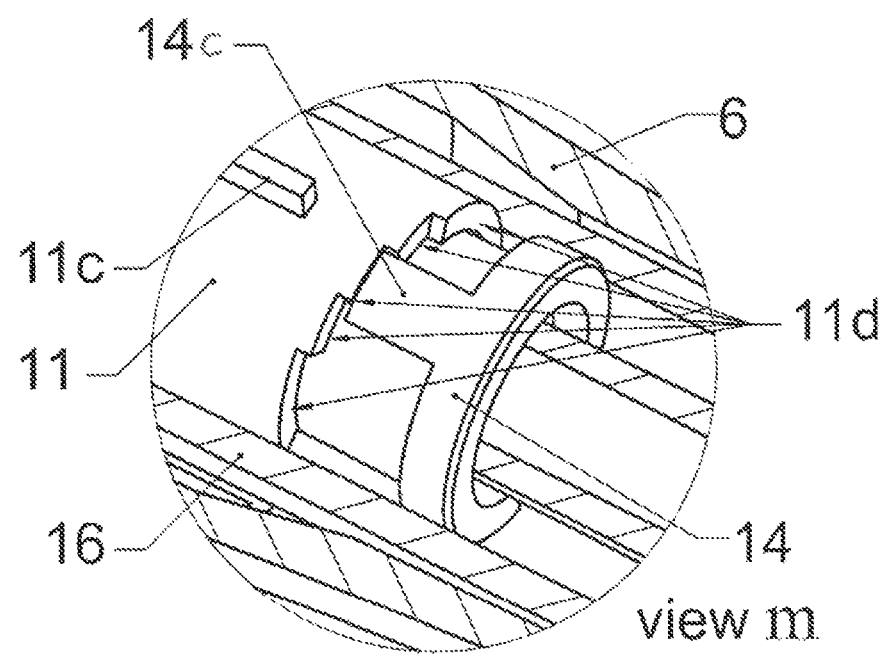

In the fifth phase (Figures from 91 to 94) the drive spring 15 is released, rapidly pushing out the driving sleeve 14 with lancet socket 7 and the lancet 17, installed in the socket 7. The ejector 8, which is sliding fitted in the guide 7b of the lancet socket 7, remains in the same position, held by the driver 9, the position of which also remains the same. The movement of the driving sleeve 14 also causes compression of the return spring 13 and ends in the moment when the bumper 14c of the driving sleeve 14 hits one of the limiting steps 11d in the back part of the mechanism body 11. These steps define the depth of the puncture in the skin with the lancet 17 that is the distance K, in which the tip of the lancet blade 17c slides out of the front part 1a of the cup 1. The bumper 14c of the driving sleeve 14 hits the limiting step 11d, directly where the bumper 14c is, as a result of the rotating motion of the driving sleeve 14, caused by rotating the button 16 when selecting the depth of the puncture (FIG. 93 and FIG. 94). In the described exemplary embodiment the differences between the heights of the adjacent limiting steps 11d equal 0.5 mm, which in result allows the user to regulate the depth of the puncture, ranging from 0.5 mm to 2.5 mm, with steps of 0.5 mm. By changing the number of the steps 11d and their pitch it is easy to adjust the range of the puncture depths, depending on the needs of various user groups. The change of the step 11d height it is possible also to compensate for the difference in lengths of various types of lancets from different manufacturers.

In the sixth phase (FIG. 95 and FIG. 96), the button 16 remains pushed in all the way, however the driving sleeve 14 with the lancet socket 7 and the lancet 17 is retracted by the return spring 13 until the moment when the tension in the return spring 13 and the drive spring 15 equalize each other. In this phase the tip of the blade 17c retracts and is covered inside the cup 1. Releasing the button 16 causes the button 16, the return spring 13, the drive spring 15 and the driving sleeve 14 with the lancet socket 7 and the lancet 17 to return to their initial positions, described above as first phase.

In order to remove the used lancet 17 the cup 1 is removed from the main body 2 by rotating it counter-clockwise and then removing it from the casing 6. Because the base 4 of the cup 1 is coupled with the driver setting 10 with two fins 4a of the cup base 4 that enter the two windows 10a of the driver setting 10. The described above rotation of the cup 1 to remove it from the main body also results in the rotation of the driver setting 10, at this point coupled with the fins 4a. The rotation of the driver setting 10 also changes the angular position of the driver 9, because it is coupled with the driver setting 10 with the drive projections 9a. Rotating the driver 9 causes it to couple with the front latches 12a of the side sliders 12. In this system the driver projections 9a can move along the guide channels 11h of the mechanism body 11, but the length of these channels is smaller than the movement range of the button 16. Pressing the button 16, and therefore also moving the side sliders 12 along with the driver 9 linked with them at the ends, is possible only until the driver projections 9a hit the front walls of the channels 11h. Thus limiting the degree to which the button 16 can be pressed, prevents activation of the puncturing device, because the activating surface 16d of the pushed button 16 is not able to release the latch 14a of the driving sleeve 14, rested on the stop surface 11a of the body 11. However, the movement range of the driver 9 is enough to move the ejector 8 on the guide 7b so far ahead that the ejector 8 goes through the window 7c in the chamber 7a and pushes the lancet 17 out of this chamber. Releasing button 16 activates the return spring 13 and the drive spring 15, what makes the ejector 8, driver 9, side sliders 12 and driving sleeve 14 with empty lancet socket 7 returns to their initial position that is to first phase described above. The reinstallation of the cup 1 in the main body 2 results in fins 4a of the cup base 4 enter first in the windows 10a of the driver setting 10 and then rotate it along with the driver 9. In the new position of the driver 9 its projections 9a are in position beyond the front latches 12a of the side sliders 12, therefore it is possible to fully press the button 16 and, if a new lancet 17 is placed in the lancet socket 7, it is possible to perform another puncture.

LIST OF DESIGNATIONS 1 cup
2 main body
3 cup sheath
3a projections inside the cup sheath 3b notch for fingers
4 cup base
4a fin
4b notch for bayonet connector with the body 11
4c notch for the inner projection 3a of the cup sheath
4d notch for lancet chamber 7a
5 mechanism unit
6 casing
6a latch channel
6b window
6c elevated shape
7 lancet socket
7a lancet chamber
7b guide
7c throughfeed window
7d latch of lancet socket
8 ejector
9 driver
9a driver projections 9b notches
9c notch for ejector 8
10 driver setting
10a window for the fin 4a
10b notch for the slider
10c notch for the driver
11 mechanism body 11a stop surface of the body
11b bayonet connector projection locking with the base 4
11c fin of the body
11d step limiting puncture depth
11e channels for side sliders
11f transversal partition
11g latch of the body
11h channel leading the driver 9 projection
12 side slider
12a front latch of the side slider
12b back latch of the side slider
13 return spring
14 driving sleeve
14a latch of the driving sleeve
14c bumper of the driving sleeve
14d axial notch for the projection 16g
15 drive spring
16 button
16a symbol indicating puncture depth
16b springy projection
16c anti-rotary channel
16d activating surface
16f notch for finger
16g projection coupling the button with the notch 14d
17 complete lancet
17a armed lancet
17b lancet blade cover
17c lancet blade

The invention claimed is:

1. A skin-puncturing device, comprising:
a main body, comprising:
  a casing in a form of a tube with a longitudinal axis, an open front end, and an open back end; and
  a mechanism unit in the casing, the mechanism unit comprising:
    a mechanism body;
    a puncturing mechanism with a lancet guiding unit;
    a puncture depth regulation mechanism; and
    a used lancet removal mechanism;
a cup configured to close the main body at the open front end of the casing;
a drive spring of the lancet guiding unit;
a one-piece driving sleeve;
a return spring of the lancet guiding unit;
a button, at the open back end of the casing, configured to tension the drive spring; and
a member configured to release the tension of the drive spring;
wherein a front end of the mechanism body is generally flush with the open front end of the casing,
wherein a back end of the mechanism body is inside the casing,
wherein the mechanism body is fixed in the casing,
wherein the lancet guiding unit comprises a lancet socket with a guide that passes through a first opening in a transverse partition of the mechanism body, from a lancet chamber at a front end of the lancet guiding unit to a front end of the driving sleeve at a back end of the lancet guiding unit,
wherein the driving sleeve as a whole is configured to:
  rotate within the casing with respect to the mechanism body;
  slide within the casing, with respect to the mechanism body, toward the open front end of the casing and toward the open back end of the casing; and
  slidingly fit in the back end of the mechanism body;
wherein the return spring is between the transverse partition of the mechanism body and the front end of the driving sleeve,
wherein the drive spring is between the driving sleeve and the button,
wherein the button is configured to rotate within the casing and is configured to slidingly fit in the open back end of the casing,
wherein the member configured to release the tension of the drive spring is a springy latch of the driving sleeve, configured to cooperate with a stop surface of the mechanism body and an activating surface of the button, and
wherein the puncture depth regulation mechanism comprises:
  the button, rotary-coupled with a back end of the driving sleeve and configured to rotate the driving sleeve;
  limiting steps formed in the back end of the mechanism body, wherein each of the limiting steps defines a relative puncture depth for selection by the driving sleeve; and
  a bumper portion of the driving sleeve configured to engage a selected one of the limiting steps, upon rotation of the driving sleeve caused by rotating the button when selecting the relative puncture depth with respect to the limiting steps, in order to limit movement of the bumper portion when the driving sleeve slides toward the open front end of the casing, and to select the relative puncture depth upon engagement between the bumper portion and the selected one of the limiting steps.

2. The device of claim 1, further comprising:
a lancet blade configured to fit in the lancet socket.

3. The device of claim 1, wherein the button comprises at least one first latch, defining a sequence of angular positions of the button upon rotation of the button in relation to the casing and defining a sequence of anti-rotary channels opposite at least one fin of the mechanism body in any angular position of the button defined by the at least one first latch,
  wherein the button is linked with two side sliders, slidingly fitted inside channels of the mechanism body,
  wherein second latches of the side sliders reach inside the mechanism body,
  wherein a driver setting is configured to rotate inside the mechanism body,
  wherein a driver with first notches for the second latches of the side sliders is configured to slide in an axial direction of the casing,
  wherein the cup comprises a longitudinal channel for the lancet chamber, and
  wherein the cup is coupled to the driver setting using one or more second notches of the cup and one or more projections of the mechanism body.

4. The device of claim 1, wherein the used lancet removal mechanism comprises:
  an ejector, slidingly fitted on the guide of the lancet socket between the lancet chamber and a driver, having a throughfeed window for the ejector in a bottom of the lancet chamber;
  the driver;
  the return spring;
  the driving sleeve; and
  the button.

5. The device of claim 1, wherein the cup comprises:
a cup sheath having a second opening for a lancet blade to facilitate puncturing of a patient's skin using the lancet blade; and
a cup base in the cup sheath;
wherein the cup base comprises an axial channel and at least one fin.

6. The device of claim 1, further comprising:
an angular position indicator of the button in relation to the casing.

7. The device of claim 6, wherein the angular position indicator of the button comprises a sequence of symbols of consecutive angular positions of the button, located circumferentially on a side surface of the casing, and
wherein when the button is released by an operator of the device, the symbols are visible via a window in the casing.

8. A skin-puncturing device, comprising:
a main body, comprising:
a casing in a form of a tube with a longitudinal axis, an open front end, and an open back end; and
a mechanism unit in the casing, the mechanism unit comprising:
a mechanism body;
a puncturing mechanism with a lancet guiding unit;
a puncture depth regulation mechanism; and
a used lancet removal mechanism;
a cup configured to close the main body at the open front end of the casing;
a drive spring of the lancet guiding unit;
a one-piece driving sleeve;
a return spring of the lancet guiding unit;
a button, at the open back end of the casing, configured to tension the drive spring;
a member configured to release the tension of the drive spring;
a lancet socket of the lancet guiding unit; and
a lancet blade in the lancet socket;
wherein a front end of the mechanism body is generally flush with the open front end of the casing,
wherein a back end of the mechanism body is inside the casing,
wherein the mechanism body is fixed in the casing,
wherein the lancet guiding unit comprises the lancet socket with a guide that passes through a first opening in a transverse partition of the mechanism body, from a lancet chamber at a front end of the lancet guiding unit to a front end of the driving sleeve at a back end of the lancet guiding unit,
wherein the driving sleeve as a whole is configured to:
rotate within the casing with respect to the mechanism body;
slide within the casing, with respect to the mechanism body, toward the open front end of the casing and toward the open back end of the casing; and
slidingly fit in the back end of the mechanism body;
wherein the return spring is between the transverse partition of the mechanism body and the front end of the driving sleeve,
wherein the drive spring is between the driving sleeve and the button,
wherein the button is configured to rotate within the casing and is configured to slidingly fit in the open back end of the casing,
wherein the member configured to release the tension of the drive spring is a springy latch of the driving sleeve, configured to cooperate with a stop surface of the mechanism body and an activating surface of the button, and
wherein the puncture depth regulation mechanism comprises:
the button, rotary-coupled with a back end of the driving sleeve and configured to rotate the driving sleeve;
limiting steps formed in the back end of the mechanism body, wherein each of the limiting steps defines a relative puncture depth for selection by the driving sleeve; and
a bumper portion of the driving sleeve configured to engage a selected one of the limiting steps, upon rotation of the driving sleeve caused by rotating the button when selecting the relative puncture depth with respect to the limiting steps, in order to limit movement of the bumper portion when the driving sleeve slides toward the open front end of the casing, and to select the relative puncture depth upon engagement between the bumper portion and the selected one of the limiting steps.

9. The device of claim 8, wherein the button comprises at least one first latch, defining a sequence of angular positions of the button upon rotation of the button in relation to the casing and defining a sequence of anti-rotary channels opposite at least one fin of the mechanism body in any angular position of the button defined by the at least one first latch,
wherein the button is linked with two side sliders, slidingly fitted inside channels of the mechanism body,
wherein second latches of the side sliders reach inside the mechanism body,
wherein a driver setting is configured to rotate inside the mechanism body,
wherein a driver with first notches for the second latches of the side sliders is configured to slide in an axial direction of the casing,
wherein the cup comprises a longitudinal channel for the lancet chamber, and
wherein the cup is coupled to the driver setting using one or more second notches of the cup and one or more projections of the mechanism body.

10. The device of claim 8, wherein the used lancet removal mechanism comprises:
an ejector, slidingly fitted on the guide of the lancet socket between the lancet chamber and a driver, having a throughfeed window for the ejector in a bottom of the lancet chamber;
the driver;
the return spring;
the driving sleeve; and
the button.

11. The device of claim 8, wherein the cup comprises:
a cup sheath having a second opening for the lancet blade to facilitate puncturing of a patient's skin using the lancet blade; and
a cup base in the cup sheath;
wherein the cup base comprises an axial channel and at least one fin.

12. The device of claim 8, further comprising:
an angular position indicator of the button in relation to the casing.

13. The device of claim 12, wherein the angular position indicator of the button comprises a sequence of symbols of consecutive angular positions of the button, located circumferentially on a side surface of the casing, and wherein when the button is released by an operator of the device, the symbols are visible via a window in the casing.

14. A skin-puncturing device, comprising:
a main body, comprising:
 a tubular casing with a longitudinal axis, a front end, and a back end; and
 a mechanism unit in the casing, the mechanism unit comprising:
  a mechanism body;
  a puncturing mechanism with a lancet guiding unit;
  a puncture depth regulation mechanism; and
  a used lancet removal mechanism;
a cup configured to close the main body at the front end of the casing;
a drive spring of the lancet guiding unit;
a one-piece driving sleeve;
a return spring of the lancet guiding unit;
a button, at the back end of the casing, configured to tension the drive spring; and
a member configured to release the tension of the drive spring;
wherein a front end of the mechanism body is generally flush with the front end of the casing,
wherein a back end of the mechanism body is inside the casing,
wherein the mechanism body is fixed in the casing,
wherein the lancet guiding unit comprises a lancet socket with a guide that passes through a first opening in a transverse partition of the mechanism body, from a lancet chamber at a front end of the lancet guiding unit to the driving sleeve at a back end of the lancet guiding unit,
wherein the driving sleeve as a whole is configured to:
 rotate within the casing with respect to the mechanism body;
 slide within the casing, with respect to the mechanism body, toward the front end of the casing; and
 slide within the casing, with respect to the mechanism body, toward the back end of the casing;
wherein the return spring is between the transverse partition of the mechanism body and the driving sleeve,
wherein the drive spring is between the driving sleeve and the button,
wherein the button is configured to rotate within the casing,
wherein the member configured to release the tension of the drive spring is a latch of the driving sleeve, configured to cooperate with a stop surface of the mechanism body and an activating surface of the button, and
wherein the puncture depth regulation mechanism comprises:
 the button, rotary-coupled with the driving sleeve and configured to rotate the driving sleeve;
 limiting steps formed in the back end of the mechanism body, wherein each of the limiting steps defines a relative puncture depth for selection by the driving sleeve; and
 a bumper portion of the driving sleeve configured to engage a selected one of the limiting steps, upon rotation of the driving sleeve caused by rotating the button when selecting the relative puncture depth with respect to the limiting steps, in order to limit movement of the bumper portion when the driving sleeve slides toward the front end of the casing, and to select the relative puncture depth upon engagement between the bumper portion and the selected one of the limiting steps.

15. The device of claim 14, further comprising:
a lancet blade configured to fit in the lancet socket.

16. The device of claim 14, wherein the button comprises at least one first latch, defining a sequence of angular positions of the button upon rotation of the button in relation to the casing and defining a sequence of anti-rotary channels opposite at least one fin of the mechanism body in any angular position of the button defined by the at least one first latch,
 wherein the button is linked with side sliders, slidingly fitted inside channels of the mechanism body,
 wherein second latches of the side sliders reach inside the mechanism body,
 wherein a driver setting is configured to rotate inside the mechanism body,
 wherein a driver with first notches for the second latches of the side sliders is configured to slide in an axial direction of the casing,
 wherein the cup comprises a longitudinal channel for the lancet chamber, and
 wherein the cup is coupled to the driver setting using one or more second notches of the cup and one or more projections of the mechanism body.

17. The device of claim 14, wherein the used lancet removal mechanism comprises:
 an ejector, slidingly fitted on the guide of the lancet socket between the lancet chamber and a driver, having a throughfeed window for the ejector in a bottom of the lancet chamber;
 the driver;
 the return spring;
 the driving sleeve; and
 the button.

18. The device of claim 14, wherein the cup comprises:
 a cup sheath having a second opening for a lancet blade to facilitate puncturing of a patient's skin using the lancet blade; and
 a cup base in the cup sheath;
 wherein the cup base comprises an axial channel and at least one fin.

19. The device of claim 14, further comprising:
 an angular position indicator of the button in relation to the casing.

20. The device of claim 19, wherein the angular position indicator of the button comprises a sequence of symbols of consecutive angular positions of the button, located circumferentially on a side surface of the casing, and
 wherein when the button is released by an operator of the device, the symbols are visible via a window in the casing.

* * * * *